(12) United States Patent
Jung et al.

(10) Patent No.: US 8,114,342 B2
(45) Date of Patent: Feb. 14, 2012

(54) METHODS AND SYSTEMS FOR MONITORING STERILIZATION STATUS

(75) Inventors: Edward K. Y. Jung, Bellevue, WA (US);
Royce A. Levien, Lexington, MA (US);
Robert W. Lord, Seattle, WA (US);
Mark A. Malamud, Seattle, WA (US);
John D. Rinaldo, Jr., Bellevue, WA (US); Lowell L. Wood, Jr., Livermore, CA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 1442 days.

(21) Appl. No.: 11/414,743

(22) Filed: Apr. 28, 2006

(65) Prior Publication Data

US 2007/0231191 A1 Oct. 4, 2007

Related U.S. Application Data

(63) Continuation-in-part of application No. 11/396,256, filed on Mar. 31, 2006, and a continuation-in-part of application No. 11/411,207, filed on Apr. 25, 2006.

(51) Int. Cl.
| | |
|---|---|
| A61L 2/24 | (2006.01) |
| F01N 3/20 | (2006.01) |
| G05B 1/00 | (2006.01) |
| G05B 9/00 | (2006.01) |
| A61L 2/28 | (2006.01) |
| G01D 11/26 | (2006.01) |
| G01N 1/00 | (2006.01) |

(52) U.S. Cl. ............... 422/3; 422/1; 422/105; 422/117; 422/119

(58) Field of Classification Search .................. 422/3, 1, 422/105, 117, 119
See application file for complete search history.

(56) References Cited

U.S. PATENT DOCUMENTS

| | | |
|---|---|---|
| 221,633 A | 10/1940 | White et al. |
| 2,689,837 A | 9/1954 | Darby et al. |
| 2,873,263 A | 2/1959 | Lal |
| 2,875,097 A | 2/1959 | Pritchard |
| 2,986,448 A | 5/1961 | Gates et al. |
| 3,325,436 A | 6/1967 | Prindle et al. |
| 3,376,110 A | 4/1968 | Shiraeff |
| 3,376,384 A | 4/1968 | Achramowicz |
| 3,480,557 A | 11/1969 | Shiraeff |
| 3,485,787 A | 12/1969 | Haefele et al. |
| 3,827,999 A | 8/1974 | Crossland |
| 3,870,783 A | 3/1975 | Hall et al. |
| 3,953,566 A | 4/1976 | Gore |
| 3,966,902 A | 6/1976 | Chromecek |
| 3,967,478 A | 7/1976 | Guinn |
| 4,042,765 A | 8/1977 | Floyd et al. |
| 4,073,764 A | 2/1978 | Hemmerich et al. |
| 4,087,925 A | 5/1978 | Bienek |
| 4,151,419 A | 4/1979 | Morris et al. |
| 4,169,123 A | 9/1979 | Moore et al. |

(Continued)

FOREIGN PATENT DOCUMENTS

CN 1638632 A 7/2005

(Continued)

OTHER PUBLICATIONS

U.S. Appl. No. 11/891,357, Jung et al.

(Continued)

*Primary Examiner* — Sean E Conley
*Assistant Examiner* — Regina M. Yoo

(57) ABSTRACT

Methods and systems for monitoring sterilization status are provided.

11 Claims, 11 Drawing Sheets

U.S. PATENT DOCUMENTS

| | | | |
|---|---|---|---|
| 4,169,124 A | 9/1979 | Forstrom et al. |
| 4,176,240 A | 11/1979 | Sabia |
| 4,187,390 A | 2/1980 | Gore |
| 4,194,041 A | 3/1980 | Gore et al. |
| 4,197,375 A | 4/1980 | Fox |
| 4,208,324 A | 6/1980 | Ramanathan |
| 4,312,907 A | 1/1982 | Hiraoka et al. |
| 4,325,870 A | 4/1982 | Bühler et al. |
| 4,369,284 A | 1/1983 | Chen |
| 4,381,380 A | 4/1983 | LeVeen et al. |
| 4,403,826 A | 9/1983 | Presby |
| 4,443,511 A | 4/1984 | Worden et al. |
| 4,476,255 A | 10/1984 | Bailey et al. |
| 4,499,154 A | 2/1985 | James et al. |
| 4,500,455 A | 2/1985 | Niwa et al. |
| 4,556,464 A | 12/1985 | St. Clair |
| 4,612,444 A | 9/1986 | Ragusa |
| 4,618,213 A | 10/1986 | Chen |
| 4,629,896 A | 12/1986 | Bridgen |
| 4,642,165 A | 2/1987 | Bier |
| 4,643,876 A | 2/1987 | Jacobs et al. |
| 4,688,585 A | 8/1987 | Vetter |
| 4,692,369 A | 9/1987 | Nomi |
| 4,716,183 A | 12/1987 | Gamarra et al. |
| 4,731,541 A | 3/1988 | Shoemaker |
| 4,744,951 A | 5/1988 | Cummings et al. |
| 4,771,482 A | 9/1988 | Shlenker |
| 4,774,324 A | 9/1988 | Loeffler et al. |
| 4,855,412 A | 8/1989 | Dehnert et al. |
| 4,855,413 A | 8/1989 | Dehnert et al. |
| 4,907,316 A | 3/1990 | Kurz |
| 4,925,732 A | 5/1990 | Driskill et al. |
| 4,935,260 A | 6/1990 | Shlenker |
| 4,935,635 A | 6/1990 | O'Harra |
| 4,942,270 A | 7/1990 | Gamarra |
| 4,943,414 A | 7/1990 | Jacobs et al. |
| 5,008,093 A | 4/1991 | Merianos |
| 5,008,106 A | 4/1991 | Merianos et al. |
| 5,030,380 A | 7/1991 | Moschner et al. |
| 5,061,106 A | 10/1991 | Kent |
| 5,069,227 A | 12/1991 | Maronian |
| 5,074,322 A | 12/1991 | Jaw |
| 5,077,047 A | 12/1991 | Biss et al. |
| 5,102,711 A | 4/1992 | Keller et al. |
| 5,113,874 A | 5/1992 | Maronian |
| 5,138,719 A | 8/1992 | Orlianges et al. |
| 5,142,010 A | 8/1992 | Olstein |
| 5,269,981 A | 12/1993 | Jameson et al. |
| 5,315,289 A | 5/1994 | Fuller et al. |
| 5,326,841 A | 7/1994 | Fellman |
| 5,357,636 A | 10/1994 | Dresdner, Jr. et al. |
| 5,360,892 A | 11/1994 | Bonsignore et al. |
| 5,403,363 A | 4/1995 | Loeffler et al. |
| 5,428,123 A | 6/1995 | Ward et al. |
| 5,459,879 A | 10/1995 | Fuchs |
| 5,480,915 A | 1/1996 | Burns |
| 5,498,394 A | 3/1996 | Matschke |
| 5,501,669 A | 3/1996 | Conway et al. |
| 5,547,635 A | 8/1996 | Duthie, Jr. |
| 5,549,924 A | 8/1996 | Shlenker et al. |
| 5,557,444 A | 9/1996 | Melville et al. |
| 5,563,238 A | 10/1996 | Bonsignore et al. |
| 5,614,151 A | 3/1997 | LeVay et al. |
| 5,641,566 A | 6/1997 | Kranzler et al. |
| H1670 H | 7/1997 | Aziz et al. |
| 5,644,798 A | 7/1997 | Shah |
| 5,648,003 A | 7/1997 | Liang et al. |
| 5,667,753 A | 9/1997 | Jacobs et al. |
| 5,688,475 A | 11/1997 | Duthie, Jr. |
| 5,731,053 A | 3/1998 | Kuhn et al. |
| 5,733,270 A | 3/1998 | Ling et al. |
| 5,779,795 A | 7/1998 | Bucher et al. |
| 5,783,290 A | 7/1998 | Isaac et al. |
| 5,786,598 A | 7/1998 | Clark et al. |
| 5,788,925 A | 8/1998 | Pai et al. |
| 5,788,940 A | 8/1998 | Cicha et al. |
| 5,798,165 A | 8/1998 | Mizoguchi et al. |
| 5,851,551 A | 12/1998 | Tseng et al. |
| 5,901,564 A | 5/1999 | Comeau, II |
| 5,920,075 A | 7/1999 | Whitehead |
| 5,945,068 A | 8/1999 | Ferone |
| 5,948,707 A | 9/1999 | Crawley et al. |
| 5,959,423 A | 9/1999 | Nakanishi et al. |
| 5,965,276 A | 10/1999 | Shlenker et al. |
| 6,010,727 A | 1/2000 | Rosenthal |
| 6,038,331 A | 3/2000 | Johnson |
| 6,132,784 A | 10/2000 | Brandt et al. |
| 6,177,677 B1 | 1/2001 | Alboresi et al. |
| 6,192,887 B1 | 2/2001 | Howett et al. |
| 6,193,931 B1 | 2/2001 | Lin et al. |
| 6,223,137 B1 | 4/2001 | McCay et al. |
| 6,252,128 B1 | 6/2001 | Obata |
| 6,254,625 B1 | 7/2001 | Rosenthal et al. |
| 6,311,974 B1 | 11/2001 | Koga |
| 6,326,654 B1 | 12/2001 | Ruden et al. |
| 6,335,529 B1 | 1/2002 | Sekii et al. |
| 6,343,425 B1 | 2/2002 | Sias et al. |
| 6,370,694 B1 | 4/2002 | Michelson |
| 6,426,701 B1 | 7/2002 | Levy et al. |
| 6,429,438 B1 | 8/2002 | Smestad |
| 6,459,955 B1 | 10/2002 | Bartsch et al. |
| 6,485,979 B1 | 11/2002 | Kippenhan et al. |
| 6,490,351 B1 | 12/2002 | Roberts |
| 6,521,552 B1 | 2/2003 | Honna et al. |
| 6,524,698 B1 | 2/2003 | Schmoock |
| 6,560,782 B2 | 5/2003 | Hourihan et al. |
| 6,573,836 B1 | 6/2003 | Gitis et al. |
| 6,577,240 B2 | 6/2003 | Armstrong |
| 6,610,254 B1 | 8/2003 | Furner et al. |
| 6,656,424 B1 | 12/2003 | Deal |
| 6,663,805 B1 | 12/2003 | Ekiner et al. |
| 6,676,871 B1 | 1/2004 | Benassi et al. |
| 6,706,243 B1 | 3/2004 | Sias et al. |
| 6,716,352 B1 | 4/2004 | Livingston |
| 6,727,818 B1 | 4/2004 | Wildman et al. |
| 6,733,495 B1 | 5/2004 | Bek et al. |
| 6,755,536 B2 | 6/2004 | Tegreene et al. |
| 6,765,029 B2 | 7/2004 | Arakawa et al. |
| 6,806,361 B1 | 10/2004 | Kajisa et al. |
| 6,872,366 B2 | 3/2005 | Thomas et al. |
| 6,901,712 B2 | 6/2005 | Lionel |
| 6,913,758 B2 | 7/2005 | Hourihan et al. |
| 6,925,679 B2 | 8/2005 | Wallach et al. |
| 6,937,221 B2 | 8/2005 | Lippert et al. |
| 6,949,222 B1 | 9/2005 | Möller et al. |
| 6,991,761 B2 | 1/2006 | Hehenberger et al. |
| 7,009,185 B2 | 3/2006 | Chi et al. |
| 7,056,971 B2 | 6/2006 | Varma |
| 7,101,408 B2 | 9/2006 | Himeno et al. |
| 7,122,150 B2 | 10/2006 | Gonzalez et al. |
| 7,175,807 B1 | 2/2007 | Jones |
| 2002/0011934 A1 | 1/2002 | Cacioli et al. |
| 2002/0085947 A1 | 7/2002 | Deal |
| 2002/0158814 A1 | 10/2002 | Bright et al. |
| 2002/0192340 A1 | 12/2002 | Swart et al. |
| 2003/0081293 A1 | 5/2003 | Wood, Jr. et al. |
| 2003/0093503 A1 | 5/2003 | Yamaki et al. |
| 2003/0145664 A1 | 8/2003 | Schwarz et al. |
| 2003/0164285 A1 | 9/2003 | Korenev |
| 2003/0170901 A1 | 9/2003 | Kippenhan et al. |
| 2003/0194344 A1 | 10/2003 | Brafford et al. |
| 2003/0235605 A1 | 12/2003 | Lelah et al. |
| 2004/0024290 A1 | 2/2004 | Root et al. |
| 2004/0056201 A1 | 3/2004 | Fink et al. |
| 2004/0090333 A1 | 5/2004 | Wildman et al. |
| 2004/0139555 A1 | 7/2004 | Conrad et al. |
| 2004/0211444 A1 | 10/2004 | Taylor et al. |
| 2004/0244138 A1 | 12/2004 | Taylor et al. |
| 2005/0013729 A1 | 1/2005 | Brown-Skrobot et al. |
| 2005/0022844 A1 | 2/2005 | Field et al. |
| 2005/0069453 A1 | 3/2005 | Forng et al. |
| 2005/0135965 A1 | 6/2005 | Williams et al. |
| 2005/0186108 A1 | 8/2005 | Fields |
| 2005/0124506 A1 | 9/2005 | Lee et al. |
| 2005/0236579 A1 | 10/2005 | Jenkins et al. |
| 2005/0249791 A1 | 11/2005 | Hobbs et al. |
| 2005/0267233 A1 | 12/2005 | Joshi |

| | | | |
|---|---|---|---|
| 2006/0071799 | A1 | 4/2006 | Verdiramo |
| 2006/0216193 | A1 | 9/2006 | Johnson et al. |
| 2006/0236496 | A1 | 10/2006 | Oh et al. |
| 2008/0184518 | A1 | 8/2008 | Taylor et al. |

FOREIGN PATENT DOCUMENTS

| | | | |
|---|---|---|---|
| EP | 0693289 A2 | 1/1996 | |
| EP | 1 537 796 A2 | 6/2005 | |
| EP | 1 609 488 A | 12/2005 | |
| EP | 1 609 488 A1 | 12/2005 | |
| GB | 2291350 A | 1/1996 | |
| JP | 1139139 | 5/1989 | |
| JP | 07289616 A | 11/1995 | |
| JP | 08071132 A | 3/1996 | |
| JP | 08071133 A | 3/1996 | |
| JP | 08215110 | 8/1996 | |
| JP | 2000220334 | 8/2000 | |
| JP | 2002364055 | 12/2002 | |
| JP | 2003250865 | 9/2003 | |
| JP | 2004317512 | 11/2004 | |
| WO | WO 95/17634 | 6/1995 | |
| WO | WO 01/10476 A1 | 2/2001 | |
| WO | WO 01/60419 A1 | 8/2001 | |
| WO | WO01/60419 A1 | 8/2001 | |
| WO | WO 03/056951 A2 | 7/2003 | |
| WO | WO 2004/032019 A2 | 4/2004 | |
| WO | WO 2004/035095 A1 | 4/2004 | |
| WO | WO2004/080494 A1 | 9/2004 | |
| WO | WO2004080494 | 9/2004 | |
| WO | WO 2005/048041 A2 | 5/2005 | |
| WO | WO2005/077076 A2 | 8/2005 | |
| WO | WO2005077076 | 8/2005 | |
| WO | WO 2006/007729 A1 | 1/2006 | |

OTHER PUBLICATIONS

Advanced Sterilization Products; "Frequently Asked Questions"; pp. 1-3; located at http://www.sterrad.com/products_&_services/sterrad/sterrad_nx/faqs/index.asp; bearing a date of 2006; printed on Mar. 3, 2006.
Big Sky Laser; "Nd:YAG & Dye Laboratory Lasers from Quantel"; pp. 1-4; located at http://www.bigskylaser.com/lablasers.html#td1190; printed on Mar. 22, 2006.
Big Sky Laser; "The Brilliant Series of Nd:YAG laser oscillators and accessories"; p. 1; located at http://www.bigskylaser.com/brilliantseries.html; printed on Mar. 22, 2006.
Enhance-It; "Mobile Room Sterilizers"; p. 1; located at http://www.enhance-it.com/06mobile.htm; bearing a date of 1999-2006; printed on Mar. 22, 2006.
Enhance-It; "Portable Germicidal Units"; p. 1; located at http://www.enhance-it.com/05portable.htm; bearing a date of 1999-2006; printed on Mar. 22, 2006.
Enhance-It, "Portable Germicidal Units". p. 1, located at http://www.enhance-it.com/04portable.htm, bearing a date of 1999-2006, printed on Mar. 22, 2006.
Enhance-It; "Ultraviolet Light"; p. 1-2; located at http://www.enhance-it.com/uaprod.htm; bearing a date of 1999-2006; printed on Mar. 22, 2006.
Globalspec; "About UV Light Systems"; pp. 1-3; located at http://light-sources.globalspec.com/LearnMore/Optics_Optical_Components/Light_Sources/Process_UV_Lamps_Systems; bearing a date of 1999-2006; printed on Mar. 22, 2006.
Hilton, Paul; "Nd:YAG laser welding"; TWI World Centre for Materials Joining Technology; pp. 1-2; located at http://www.twi.co.uk/i32k/protected/band_3/kspah003.html; bearing a date of 2001; printed on Mar. 22, 2006.
Medical Device Link; "Equipment News: Packaging and Sterilization Equipment—Machine Designers Address Space, Validation Issues"; Medical Product Manufacturing News; pp. 1-5; located at http://www.devicelink.com/mpmn/archive/01/04/004.html; bearing a date of Apr. 2001; printed on Mar. 22, 2006.
Nehmzow, U.; "Mobile Robotics: A Practical Introduction," 2nd Edition, 2003, ISBN No. 1852337265, Springer, London, UK.
Siegwart, Roland; Nourbakhsh, Illah R.; "Introduction to Autonomous Mobile Robots," 2004, ISBN No. 0-262-19502-X, The MIT Press, Cumberland, RI.
Wikipedia; "Nd:YAG laser"; pp. 1-2; located at http://en.wikipedia.org/wiki/Nd-YAG_laser; bearing a date of Feb. 23, 2006; printed on Mar. 22, 2006.
Xenon Corporation; "SteriPulse-XL-Sterilization and Decontamination Systems"; pp. 1-6; located at http://www.xenoncorp.com/sterilization.html; printed on Mar. 23, 2006.
Xie, Ming; "Fundamentals of Robotics: Linking Perception to Action," 2003, ISBN No. 9812383131, World Scientific Publishing Co. Pte. Ltd., River Edge, NJ.
Creative Concepts; "Creative Oz-Air (i) Pvt. Ltd: Ozone Ambient Air Monitor & Controller, Hands Sterilizer, U.V. Systems, Ozone Test Kits, Ozone Accessories"; pp. 1-3; Creative Oz-Air (i) Pvt. Ltd.; located at http://www.creativeconceptsozair.com/ozoneambient.html#handstenlizer; printed on Apr. 25, 2006.
De Kock, Servaas; "Marketplace: Ozone Dry hand Sterilizing Unit"; pp. 1-2; located at http://www.ecademy.com/module.php?mod=list&lid=11053; bearing a date of Dec. 3, 2005; Ecademy; Cape Town, South Africa, printed on Mar. 25, 2006.
Elgan, Mike; "The Raw Feed Archives: Unexpected Convergence: Mouse and Hand Sterilizer"; pp. 1-6; located at http://www.mikeslist.com/2003_09_28_archive.html; bearing a date of Oct. 4, 2003; Mike's List; printed on Apr. 25, 2006.
HRS; "Specialty/Hygiene System—Hand Sterilizer" pp. 1-2; located at http://www.hrs.co.kr/english/hrs_specialty_hand.htm; bearing a date of 2004; HRS, Seoul, South Korea; printed on Apr. 25, 2006.
Marhoc; "Marhoc's Automatic Hand Sterilizer U.S. Patent # - 6,872,366" pp. 1-3; located at http://www.marhoc.com/Marhoc_Hand_Sterilizer.htm; bearing a date of 2005; Marhoc, printed on Apr. 25, 2006.
Olgear; "Ozone Dry Hand Sterilising unit"; pp. 1-2; located at http://www.olgear.com/sites/58/images/ozone_hand_steriliser.pdf.
Tidybio; "No-touch fully inductive control: Quick-speed and efficient sterilization: No need of water supply and quick-speed air-drying: Easy Operation without waste"; pp. 1-7; located at http://www.tidybio.cn/english/Sterilizer.shtml; bearing a date of 2003-2005; Beijing Tidybio Science & Technology Co., Ltd., printed on Apr. 25, 2006.
PCT International Search Report; International App. No. PCT/US 07/23129; Apr. 10, 2008; pp. 1-2.
PCT International Search Report; International App. No. PCT/US 07/07582; Apr. 11, 2008; pp. 1-2.
U.S. Appl. No. 11/442,688, filed May 26, 2006, Jung et al.
U.S. Appl. No. 11/442,699, filed May 26, 2006, Jung et al.
U.S. Appl. No. 11/440,460, filed May 23, 2006, Jung et al.
U.S. Appl. No. 11/593,193, Jung et al.
U.S. Appl. No. 11/592,010, Ishikawa et al.
U.S. Appl. No. 11/584,435, Jung et al.
U.S. Appl. No. 11/584,339, Hyde et al.
"CDC Urges Hospitals to Tackle Drug-Resistant Infections"; The Wall Street Journal; bearing a date of Oct. 19, 2006; pp. 1-2; printed on Oct. 31, 2006.
Smith, Ann; Heckelman, Patricia E.; O'Neil, Maryadele J. (Ed); Budavari, Susan (Ed); The Merck Index: An Encyclopedia of Chemicals, Drugs and Biologicals; bearing a date of Oct. 2001; 2564 pages; 13th Edition; ISBN No. 0911910131; John Wiley and Sons and Merck & Co. Inc.; Whitehouse Station, NJ (not provided).
Smith, Michael; "ICAAC: Rhinovirus on Hands Blocked By Solution for Hours"; MedPage Today; Bearing dates of Oct. 2, 2006 and 2004-2006; pp. 1-2; San Francisco; MedPage Today, LLC; printed on Oct. 19, 2006.
PCT International Search Report; International App. No. PCT/US 07/07846, Nov. 18, 2008, pp. 1-2.
PCT International Search Report; International App. No. PCT/US07/07673, Oct. 10, 2008, pp. 1-2.
PCT International Search Report; International App. No. PCT/US07/07845, Sep. 18, 2008, pp. 1-2.
U.S. Appl. No. 12/384,168, Jung et al.
U.S. Appl. No. 12/384,166, Jung et al.
U.S. Appl. No. 60/605066, filed Aug. 27, 2004, Taylor, Charles E.
European Search Report; European App. No. EP 07 75 4150; Sep. 14, 2009; pp. 1-6.
U.S. Appl. No. 12/587,143, Jung et al.
U.S. Appl. No. 12/587,142, Jung et al.

U.S. Appl. No. 12/587,104, Hyde et al.
Supplementary European Search Report; European App. No. 07774171.8; Sep. 14, 2009; 6 Total Pages.
Supplementary European Search Report; European App. No. 07754226.4; Sep. 14, 2009; 7 Total Pages.
Supplementary European Search Report; European App. No. 07754375.9; Sep. 14, 2009; 6 Total Pages.
Supplementary European Search Report; European App. No. 07754150.6; Sep. 14, 2009; 6 Total Pages.
State Intellectual Property Office of P.R.C.; Application No. 200780040949.2; Jul. 16, 2010; pp. 1-7.
U.S. Appl. No. 12/800,814, Hyde et al.
UK Intellectual Property Office Examination Report Under Section 18(3); App. No. GB0908938.4; Mar. 1, 2011; pp. 1-5.

METHODS AND SYSTEMS FOR MONITORING STERILIZATION STATUS

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

For purposes of the USPTO extra-statutory requirements, the present application constitutes a continuation-in-part of U.S. patent application Ser. No. 11/396,256, entitled STERILIZATION METHODS AND SYSTEMS, naming Edward K. Y. Jung, Royce A. Levien, Robert W. Lord, Mark A. Malamud, John D. Rinaldo, Jr., and Lowell L. Wood, Jr. as inventors, filed 31 Mar. 2006, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/411,207, entitled SURVEYING STERILIZER METHODS AND SYSTEMS, naming Roderick A. Hyde, Edward K. Y. Jung, Royce A. Levien, Robert W. Lord, Mark A. Malamud, John D. Rinaldo, Jr., Clarence T. Tegreene, and Lowell L. Wood Jr. as inventors, filed 25 Apr. 2006, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, *Benefit of Prior-Filed Application*, USPTO Official Gazette Mar. 18, 2003, available at http://www.uspto.gov/web/offices/com/sol/og/2003/week11/patbene.htm. The present applicant entity has provided above a specific reference to the application(s) from which priority is being claimed as recited by statute. Applicant entity understands that the statute is unambiguous in its specific reference language and does not require either a serial number or any characterization, such as "continuation" or "continuation-in-part," for claiming priority to U.S. patent applications. Notwithstanding the foregoing, applicant entity understands that the USPTO's computer programs have certain data entry requirements, and hence applicant entity is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

TECHNICAL FIELD

The present disclosure relates to methods and systems that may be used for monitoring sterilization status within numerous contexts, such as health-care and manufacturing facilities.

SUMMARY

In some embodiments, a method is provided that includes comparing one or more sterilization statuses associated with one or more objects to one or more sterilization levels associated with one or more spaces and generating one or more signals in response to the comparing. In addition to the foregoing, other method aspects are described in the claims, drawings, and text forming a part of the present disclosure.

In some embodiments, a method is provided that includes receiving one or more signals generated in response to comparing one or more sterilization statuses associated with one or more objects to one or more sterilization levels associated with one or more spaces and responding to the receiving. In addition to the foregoing, other method aspects are described in the claims, drawings, and text forming a part of the present disclosure.

In some embodiments, a system is provided that includes circuitry for comparing one or more sterilization statuses associated with one or more objects to one or more sterilization levels associated with one or more spaces and circuitry for generating one or more signals in response to the comparing. In addition to the foregoing, other system aspects are described in the claims, drawings, and text forming a part of the present disclosure.

In some embodiments, a system is provided that includes circuitry for receiving one or more signals generated in response to comparing one or more sterilization statuses associated with one or more objects to one or more sterilization levels associated with one or more spaces and circuitry for responding to the receiving. In addition to the foregoing, other system aspects are described in the claims, drawings, and text forming a part of the present disclosure.

In some embodiments, a system is provided that includes means for comparing one or more sterilization statuses associated with one or more objects to one or more sterilization levels associated with one or more spaces and means for generating one or more signals in response to the comparing. In addition to the foregoing, other system aspects are described in the claims, drawings, and text forming a part of the present disclosure.

In some embodiments, a system is provided that includes means for receiving one or more signals generated in response to comparing one or more sterilization statuses associated with one or more objects to one or more sterilization levels associated with one or more spaces and means for responding to the receiving. In addition to the foregoing, other system aspects are described in the claims, drawings, and text forming a part of the present disclosure.

In one or more various aspects, related systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer. In addition to the foregoing, other system aspects are described in the claims, drawings, and text forming a part of the present disclosure.

The foregoing summary is illustrative only and is not intended to be in any way limiting. In addition to the illustra-

DETAILED DESCRIPTION

Figure 1:
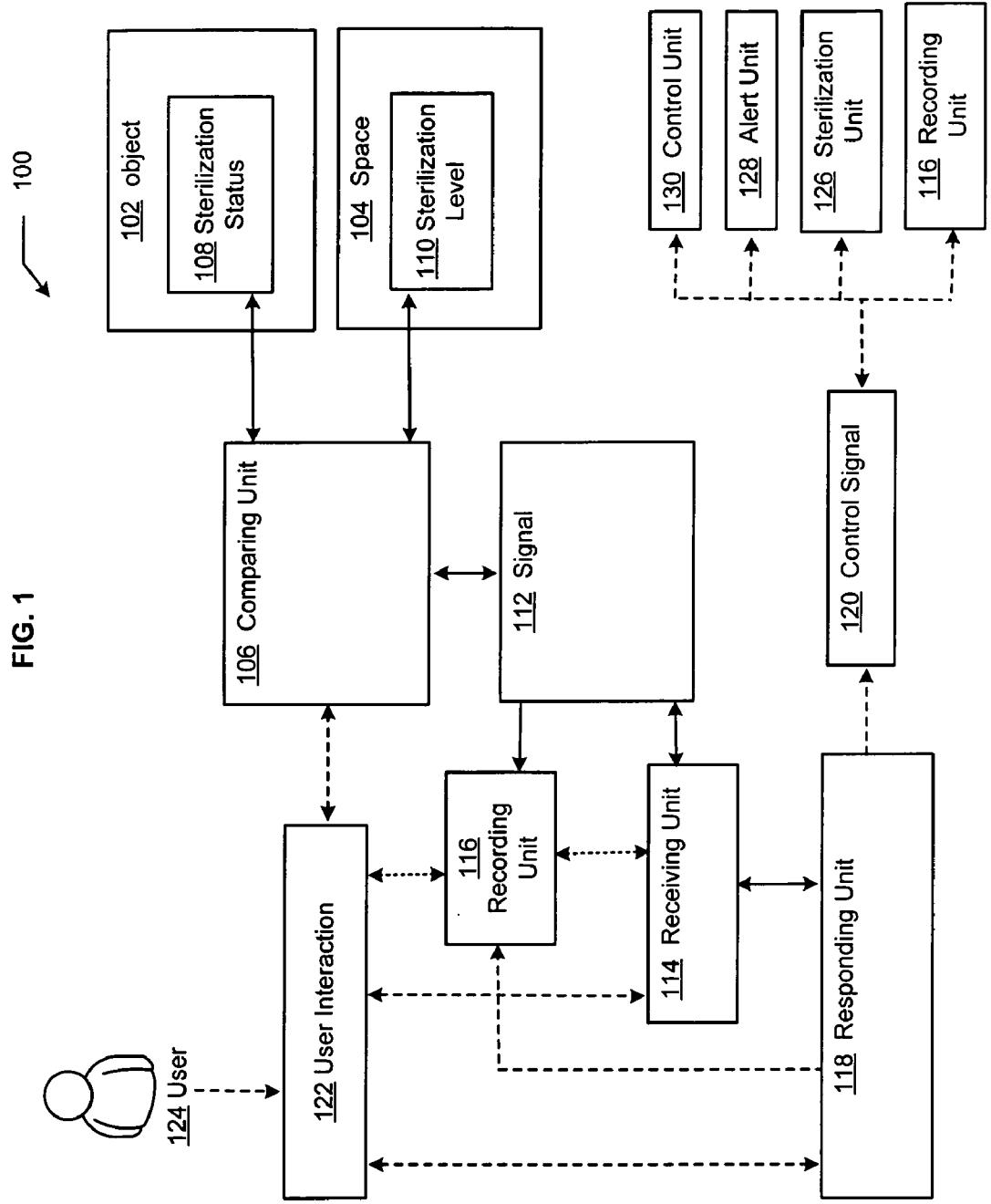
FIG. 1 illustrates an example system 100 in which embodiments may be implemented.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

FIG. 1 illustrates an example system 100 in which embodiments may be implemented. In some embodiments, the system 100 is operable to provide a method that may be used to monitor sterilization status. In some embodiments, the system 100 is operable to provide a method that may be used to facilitate entry of one or more objects 102 into one or more spaces 104. In some embodiments, the system 100 is operable to provide a method that may be used to prohibit entry of one or more objects 102 into one or more spaces 104. In some embodiments, the system 100 is operable to provide a method that may be used to track movement of one or more objects 102. In some embodiments, the system 100 is operable to provide a method that may be used to record movement of one or more objects 102. In some embodiments, the system 100 is operable to provide a method that may be used to record one or more sterilization statuses of one or more objects 102. In some embodiments, the system 100 is operable to provide a method that may be used to promote the sterilization of one or more objects 102. In some embodiments, the system 100 is operable to provide a method that may be used to promote sterilization of one or more spaces 104. In some embodiments, the system 100 is operable to provide a method that may be used to prohibit entry of one or more non-sterile objects 102 into one or more spaces 104. In some embodiments, the system 100 is operable to provide a method that may be used to prohibit entry of one or more non-sterile objects 102 into one or more sterile spaces 104. In some embodiments, the system 100 is operable to provide a method that may be used to prohibit entry of one or more sterile objects 102 into one or more non-sterile spaces 104. In some embodiments, the system 100 is operable to provide a method that may be used to prohibit reuse of one or more objects 102. In some embodiments, the system 100 is operable to provide a method that may be used to promote reuse of one or more objects 102 following sterilization of the one or more objects 102. In some embodiments, the system 100 is operable to provide a method that may be used to prohibit entry of one or more humans into one or more spaces 104. In some embodiments, the system 100 is operable to provide a method that may be used to promote entry of one or more humans into one or more spaces 104. In some embodiments, the system 100 is operable to provide a method that may be used to prohibit entry of one or more humans into one or more spaces 104 that include one or more humans. In some embodiments, the system 100 is operable to provide a method that may be used to promote entry of one or more humans into one or more spaces 104 that include one or more humans.

Comparing Unit

The system 100 may include one or more comparing units 106. In some embodiments, one or more comparing units 106 can detect one or more sterilization statuses 108 that are associated with one or more objects 102. In some embodiments, one or more comparing units 106 can detect one or more sterilization levels 110 that are associated with one or more spaces 104. In some embodiments, one or more comparing units 106 can compare one or more sterilization statuses 108 that are associated with one or more objects 102 to one or more sterilization levels 110 that are associated with one or more spaces 104. In some embodiments, the one or more comparing units 106 can determine if one or more sterilization statuses 108 are above one or more values associated with one or more sterilization levels 110. In some embodiments, the one or more comparing units 106 can determine if one or more sterilization statuses 108 are below one or more values associated with one or more sterilization levels 110. In some embodiments, the one or more comparing units 106 can determine if one or more sterilization statuses 108 are within a range of values associated with one or more sterilization levels 110. In some embodiments, multiple sterilization levels 110 may be associated with one or more spaces 104. Accordingly, in some embodiments, one or more comparing units 106 can compare one or more sterilization statuses 108 associated with one or more objects 102 to one or more sterilization levels 110 associated with one or more spaces 104. Comparing units 106 can utilize numerous technologies to detect one or more sterilization statuses 108 associated with one or more objects 102. For example, in some embodiments, comparing units 106 can detect fluorescent indicators, radio frequency signals, magnetic properties, color changes of chemical indicators, bar codes, and the like. Use of such detection methods are known and have been described (i.e., U.S. Pat. No. 6,485,979: Electronic system for tracking and monitoring articles to be sterilized and associated method, herein incorporated by reference). In some embodiments, comparing units 106 may utilize technologies that include, but are not limited to, motion detectors, infrared detectors, retinal scanners, weight detectors, and the like. In some embodiments, one or more comparing units 106 can change the sterilization status 108 associated with one or more objects 102. In some embodiments, one or more comparing units 106 can change the sterilization status 108 associated with one or more objects 102 after the one or more objects 102 have been sterilized. Accordingly, in some embodiments, one or more comparing units 106 can change the sterilization status 108 associated with one or more objects 102 that were initially associated with a low sterilization status 108 to a high sterilization status 108 after the one or more objects 102 were sterilized. In some embodiments, one or more comparing units 106 can change the sterilization status 108 associated with one or more objects 102 that were initially associated with a high sterilization status 108 to a low sterilization status 108 after the one or more objects 102 were exposed to a non-sterile space 104. Accordingly, in some embodiments, one or more comparing units 106 may change one or more sterilization statuses 108 associated with one or more objects 102 to substantially any sterilization status 108. Comparing units 106 may be configured in numerous ways. Examples of such configurations include, but are not limited to, bracelets, rings, cards, necklaces, badges and the like.

In some embodiments, one or more comparing units 106 may detect one or more objects 102 with which one or more sterilization statuses 108 have not been associated. Accordingly, in some embodiments, one or more comparing units 106 may generate one or more signals 112 indicating entry, exit and/or substantially any combination thereof of one or more objects 102 into, or out of, one or more spaces 104. For example, in some embodiments, one or more comparing units 106 may detect entry of an object 102, such as a mouse, that has not been associated with one or more sterilization statuses 108 into, or out of, one or more spaces 104. Accordingly, the one or more comparing units 106 may generate one or more signals 112 indicating entry, exit, or substantially any combination thereof of the object 102, such as the mouse, from the one or more spaces 104. In some embodiments, the one or more signals 112 may be associated with one or more recording units 116 to record the presence of the one or more objects 102, such as the mouse, within the one or more spaces 104. In some embodiments, the one or more signals 112 may be associated with one or more alert units 128 to indicate the presence of the one or more objects 102, such as the mouse, within the one or more spaces 104. In some embodiments, one or more comparing units 106 will associate one or more non-sterile statuses 108 to one or more objects 102 that have not previously been associated with one or more sterilization statuses 108. For example, in some embodiments, one or more comparing units 106 may detect entry of a fly into one or more spaces 104 and may associate one or more non-sterile sterilization statuses 108 with the fly. Accordingly, in some embodiments, one or more comparing units 106 may generate one or more signals 112 indicating entry of a non-sterile fly into one or more spaces 104. Such signals 112 may be associated with one or more recording units 116 and/or one or more alert units 128 to record and/or indicate the presence of the fly within the one or more spaces 104.

Sterilization Status

Numerous criteria may be used to associate one or more sterilization statuses 108 with one or more objects 102. Such criteria include, but are not limited to, the identity of an object 102, the length of time that an object 102 was sterilized, the type of sterilizing agent used to sterilize an object 102, the last time that an object 102 was sterilized, the number of times that an object 102 has been used, the number of times that an object 102 has been sterilized, the frequency with which an object 102 is sterilized, the purpose for which an object 102 is used, the type of contamination to which an object 102 was exposed, and/or substantially any combination thereof. In some embodiments, the sterilization status 108 associated with an object 102 may indicate that the object 102 is non-sterile. In some embodiments, the sterilization status 108 associated with an object 102 may indicate that the object 102 is sterile. In some embodiments, the sterilization status 108 associated with an object 102 may indicate that the object 102 is sterile with regard to one or more types of contamination. In some embodiments, the sterilization status 108 associated with an object 102 may indicate that the object 102 is non-sterile with regard to one or more types of contamination. For example, an object 102 may be sterile with regard to a bacterial contaminant but not sterile with regard to contamination with a prion. In some embodiments, sterile or non-sterile sterilization status 108 may be associated with one or more objects 102 according to a relative scale. For example, in some embodiments, one or more objects 102 may be associated with sterile status if it is thought that there is less than one surviving microorganism per one million objects 102 that have been sterilized (i.e., sterilization assurance level defined by European Standard EN556). In some embodiments, one or more sterilization statuses 108 may be defined and verified through use of known standards and methods, such as those put forth by the International Standards Organization (i.e., ISO 11137 and ISO 11135). In some embodiments, a numerical scale may be used to associate one or more sterilization statuses 108 with one or more objects 102. For example, in some embodiments, a range of numbers from zero to ten may be used to define one or more sterilization statuses 108 associated with one or more objects 102. In some embodiments, a range of numbers from zero to one hundred may be used to define one or more sterilization statuses 108 associated with one or more objects 102. Accordingly, substantially any numerical range may be used to define one or more sterilization statuses 108 associated with one or more objects 102. In some embodiments, sterilization status 108 may be defined through use of relative terms. Examples of such terms include, but are not limited to, sterile, non-sterile, very low, low, medium, high, very high and the like.

Numerous technologies may be used to indicate one or more sterilization statuses 108. Examples of such technologies include, but are not limited to, use of fluorescent indicators, radio frequency signals, magnetic properties, color changes of chemical indicators, and bar codes which may be used to indicate one or more sterilization statuses 108. Such technologies are known and have been described (i.e., U.S. Pat. No. 6,485,979: Electronic system for tracking and monitoring articles to be sterilized and associated method, herein incorporated by reference). These, and other, technologies may be configured in numerous ways that include, but are not limited to, bracelets, rings, cards, necklaces, badges and the like. In some embodiments, such technologies may be associated with one or more objects 102.

Sterilization Level

Numerous criteria may be used to associate one or more sterilization levels 110 with one or more spaces 104. Such criteria include, but are not limited to, the length of time that a space 104 was sterilized, the type of sterilizing agent used to sterilize the space 104, the last time that the space 104 was sterilized, the number of times that the space 104 has been used, the number of times that the space 104 has been sterilized, the frequency with which the space 104 is sterilized, the purpose for which the space 104 is used, the type of contamination to which the space 104 is exposed and/or substantially any combination thereof. In some embodiments, the sterilization level 110 associated with a space 104 may indicate that the space 104 is non-sterile. In some embodiments, the sterilization level 110 associated with a space 104 may indicate that the space 104 is sterile. In some embodiments, the sterilization level 110 associated with a space 104 may indicate that the space 104 is sterile with regard to one or more types of contamination. In some embodiments, the sterilization level 110 associated with a space 104 may indicate that the space 104 is non-sterile with regard to one or more types of contamination. For example, a space 104 may be sterile with regard to a bacterial contaminant but non-sterile with regard to contamination with a prion. In some embodiments, one or more spaces 104 may be associated with one or more sterilization levels 110 according to a standard (i.e., sterilization assurance level defined by European Standard EN556). In some embodiments, one or more sterilization levels 110 can be defined and verified through use of known standards and methods, such as those put forth by the International Standards Organization (i.e., ISO 11137 and ISO 11135).

In some embodiments, a numerical scale may be used to associate one or more sterilization levels 110 with one or more spaces 104. For example, in some embodiments, a range of numbers from zero to ten may be used to define one or more sterilization levels 110 associated with one or more spaces 104. In some embodiments, a range of numbers from zero to one hundred may be used to define one or more sterilization levels 110 associated with one or more spaces 104. Accordingly, substantially any numerical range may be used to define one or more sterilization levels 110 associated with one or more spaces 104. In some embodiments, one or more sterilization levels 110 may be defined through use of relative terms. Examples of such relative terms include, but are not limited to, very low, low, high-low, low-medium, medium, high-medium, low-high, high, very high and the like. In some embodiments, one or more compliance ranges can be associated with one or more sterilization levels 110. For example, in some embodiments, a first compliance range may be associated with one or more first types of contamination and a second compliance range may be associated with one or more second types of contamination. In some embodiments, one compliance range is associated with one sterilization level I 10. In some embodiments, one compliance range is associated with one or more sterilization levels 110. In some embodiments, a compliance range may be defined to include a minimum value and values above the minimum value. For example, in some embodiments, a space 104 may be associated with sterilization levels 110 having a range of zero to ten and a compliance range having values of seven and above. Accordingly, objects 102 associated with a sterilization status 108 having a value of seven or above may enter into the space 104 in compliance with the compliance range associated with the space 104. In contrast, objects 102 associated with a sterilization status 108 having a value that is less than seven are outside of the compliance range and entry of such objects 102 into the space 104 is in noncompliance with the compliance range associated with the sterilization level 110.

In some embodiments, a compliance range may be defined to include a maximum value and values below the maximum value. For example, in some embodiments, a space 104 may be associated with sterilization levels 110 having a range of zero to ten and a compliance range having values of three and below. Accordingly, objects 102 associated with a sterilization status 108 having a value of three or below may enter into the space 104 in compliance with the compliance range associated with the space 104. In contrast, objects 102 associated with a sterilization status 108 having a value that is greater than three are outside of the compliance range and entry of such objects 102 into the space 104 is in noncompliance with the compliance range associated with the sterilization level 110. In some embodiments, a compliance range may be defined to include a minimum value, a maximum value, and values between the minimum and maximum values. For example, in some embodiments, a space 104 may be associated with sterilization levels 110 having a range of zero to ten and a compliance range having values of three to seven. Accordingly, objects 102 associated with a sterilization status 108 having values of three, seven, and values between three and seven, may enter into the space 104 in compliance with the compliance range associated with the space 104. In contrast, objects 102 associated with a sterilization status 108 having a value that is less than three or greater than seven are outside of the compliance range and entry of such objects 102 into the space 104 is in noncompliance with the compliance range associated with the sterilization level 110.

In some embodiments, a compliance range may be defined to include a range of relative values. For example, in some embodiments, a space may be associated with sterilization levels 110 having a range of relative values that are low to high and a compliance range that includes a medium relative value and higher. Accordingly, objects 102 associated with a sterilization status 108 having values of medium or higher may enter into the space 104 in compliance with the compliance range associated with the space 104. In contrast, objects 102 associated with a sterilization status 108 having relative values that are less than medium are outside of the compliance range and entry of such objects 102 into the space 104 is in noncompliance with the compliance range associated with the sterilization level 110.

In some embodiments, a space may be associated with sterilization levels 110 having a range of relative values that are low to high and a compliance range that includes a medium relative value and lower. Accordingly, objects 102 associated with a sterilization status 108 having values of medium or lower may enter into the space 104 in compliance with the compliance range associated with the space 104. In contrast, objects 102 associated with a sterilization status 108 having relative values that are greater than medium are outside of the compliance range and entry of such objects 102 into the space 104 is in noncompliance with the compliance range associated with the sterilization level 110.

In some embodiments, a compliance range may be defined to include a range of relative values that include a minimum and a maximum. For example, in some embodiments, a space may be associated with sterilization levels 110 having a range of relative values that are low to high and a compliance range that includes low-medium to high-medium relative values. Accordingly, objects 102 associated with a sterilization status 108 having values of low-medium to high-medium may enter into the space 104 in compliance with the compliance range associated with the space 104. In contrast, objects 102 associated with a sterilization status 108 having relative values that are greater than high-medium or less than low-medium are outside of the compliance range and entry of such objects 102 into the space 104 is in noncompliance with the compliance range associated with the sterilization level 110.

Numerous technologies may be used to indicate one or more sterilization levels 110. Examples of such technologies include, but are not limited to, use of fluorescent indicators, radio frequency signals, magnetic properties, color changes of chemical indicators, and bar codes which may be used to indicate one or more sterilization levels 110. Such technologies are known and have been described (i.e., U.S. Pat. No. 6,485,979: Electronic system for tracking and monitoring articles to be sterilized and associated method, herein incorporated by reference). These, and other, technologies may be configured in numerous ways that include, but are not limited to, bracelets, rings, cards, necklaces, badges and the like. In some embodiments, such technologies may be associated with one or more spaces 104.

Space

System 100 may be used to monitor numerous spaces 104. Examples of spaces 104 include, but are not limited to, hospitals, pharmaceutical production facilities, food preparation and/or packaging facilities, dental offices, medical offices, operating rooms, veterinary clinics, medical examination rooms, and the like. In some embodiments, a space 104 is a human body. In some embodiments, a space 104 is a non-human body. In some embodiments, one or more sterilization levels 110 may be associated with one or more spaces 104. For example, a hospital waiting room may be associated with a lower sterilization level 110 than a hospital operating room. In some embodiments, one or more sterilization levels 110 may be associated with one or more spaces 104 based on the identity of the one or more spaces 104. For example, in some embodiments, the one or more spaces 104 may be part of a human, or non-human, body.

Object

System 100 may include numerous types of objects 102 that may be used in numerous industries. In some embodiments, the objects 102 are related to the food industry. Examples of such objects 102 include, but are not limited to, food containers, utensils, food service workers, and the like. In some embodiments, the objects 102 are related to the pharmaceutical industry. Examples of such objects 102 include, but are not limited to, pharmaceutical packaging, pharmaceutical workers, machinery, and the like. In some embodiments, the objects 102 are related to the medical industry. Examples of such objects 102 include, but are not limited to, gloves, medical instruments, dental instruments, containers, tools, food, humans, non-human animals, parts of a human such as hands, hospital equipment, and the like.

Signal

System 100 may include one or more signals 112. Numerous technologies can be used to produce one or more signals within system 100. For example, in some embodiments, signals 112 may be radio frequency signals, magnetic signals, infrared signals, digital signals, analog signals, and the like. In some embodiments, one or more receiving units 114 may receive one or more signals 112 from one or more comparing units 106. In some embodiments, one or more signals 112 are received by one or more recording units 116.

Receiving Unit

System 100 may include one or more receiving units 114. In some embodiments, one or more receiving units 114 receive one or more signals 112 from one or more comparing units 106. In some embodiments, one or more receiving units 114 communicate with one or more recording units 116. In some embodiments, one or more receiving units 114 can communicate with one or more responding units 118. In some embodiments, one or more users 124 may interact with one or more receiving units 114 through user interaction 122.

Recording Unit

System 100 may include one or more recording units 116. In some embodiments, one or more recording units 116 receive one or more signals 112 from one or more comparing units 106. In some embodiments, one or more recording units 116 communicate with one or more receiving units 114. In some embodiments, one or more recording units 116 communicate with one or more responding units 118. In some embodiments, one or more users 124 may interact with one or more recording units 116 through user interaction 122. In some embodiments, one or more recording units 116 may record one or more spaces 104 where one or more objects 102 have entered. In some embodiments, one or more recording units 116 may record one or more spaces 104 where one or more objects 102 have not entered. In some embodiments, one or more recording units 116 may record when one or more objects 102 have been sterilized. In some embodiments, one or more recording units 116 may record the frequency with which one or more objects 102 have been sterilized. In some embodiments, one or more recording units 116 may record one or more sterilization methods used to sterilize one or more objects 102. In some embodiments, one or more recording units 116 may record one or more sterilization levels 110 that have been assigned to one or more spaces 104. In some embodiments, one or more recording units 116 may record changes made to one or more sterilization levels 110 that have been associated with one or more spaces 104. In some embodiments, one or more recording units 116 may record changes made to one or more sterilization statuses 108 that have been associated with one or more objects 102. In some embodiments, one or more recording units 116 may record if one or more sterilization statuses 108 associated with one or more objects 102 are within one or more ranges of values associated with one or more sterilization levels 110. In some embodiments, one or more recording units 116 may record if one or more sterilization statuses 108 associated with one or more objects 102 are outside one or more ranges of values associated with one or more sterilization levels 110.

Responding Unit

System 100 may include one or more responding units 118. In some embodiments, one or more responding units 118 communicate with one or more receiving units 114. In some embodiments, one or more responding units 118 communicate with one or more recording units 116. In some embodiments, one or more users 124 can interact with one or more responding units 118 through user interaction 122. In some embodiments, one or more responding units 118 can generate one or more control signals 120. Numerous technologies can be used to generate one or more control signals 120 within system 100. For example, in some embodiments, control signals 120 may be radio frequency signals, magnetic signals, infrared signals, digital signals, analog signals, and the like. In some embodiments, one or more responding units 118 can change the sterilization status 108 associated with one or more objects 102. In some embodiments, one or more responding units 118 can change the sterilization level 110 associated with one or more spaces 104.

Control Signal

System 100 may include one or more control signals 120. In some embodiments, one or more control signals 120 are associated with one or more sterilization units 126. In some embodiments, one or more control signals 120 are associated with one or more recording units 116. In some embodiments, one or more control signals 120 are associated with one or more alert units 128. In some embodiments, one or more control signals 120 are associated with one or more control units 130. In some embodiments, one or more control signals 120 are generated by one or more responding units 118.

Sterilization Unit

System 100 may include one or more sterilization units 126. Numerous types of sterilization units 126 may be used within system 100. Examples of such sterilization units 126 include, but are not limited to, those that utilize chemicals, ultraviolet light, gamma radiation, sonic radiation, heat, and the like to sterilize an object 102 or space 104. In some embodiments, one or more sterilization units 126 can sterilize one or more objects 102 in response to a control signal 120 received from one or more responding units 118. In some embodiments, one or more sterilization units 126 can sterilize one or more spaces 104 in response to a control signal 120 received from one or more responding units 118. In some embodiments, one or more sterilization units 126 can change the sterilization status 108 of one or more objects 102.

Alert Unit

System 100 may include one or more alert units 128. In some embodiments, one or more alert units 128 can indicate if one or more objects 102 have one or more sterilization statuses 108 that are outside one or more ranges of values associated with one or more sterilization levels 110 associated with one or more spaces 104. In some embodiments, one or more alert units 128 can indicate if one or more objects 102 have one or more sterilization statuses 108 that are within one or more ranges of values associated with one or more sterilization levels 110 associated with one or more spaces 104.

Control Unit

System 100 may include one or more control units 130. Control units 130 may be coupled to numerous devices to provide for control of the devices by system 100. For example, in some embodiments, one or more control units 130 can be coupled to one or more door locks to allow one or more objects 102 to enter into, or exit from, one or more spaces 104.

User Interaction

The system 100 may provide for user interaction 122. In some embodiments, a user 124 may interact with one or more responding units 118, one or more recording units 116, one or more receiving units 114, one or more comparing units 106, one or more sterilization units 126, one or more alert units 128, one or more control units 130 and/or substantially any combination thereof. The user 124 can interact through use of numerous technologies. For example, user interaction 122 can occur through use of hardwired methods, such as through use of a keyboard, use of wireless methods, use of the internet, and the like. In some embodiments, a user 124 is human. In some embodiments, a user 124 is not human.

Figure 2:
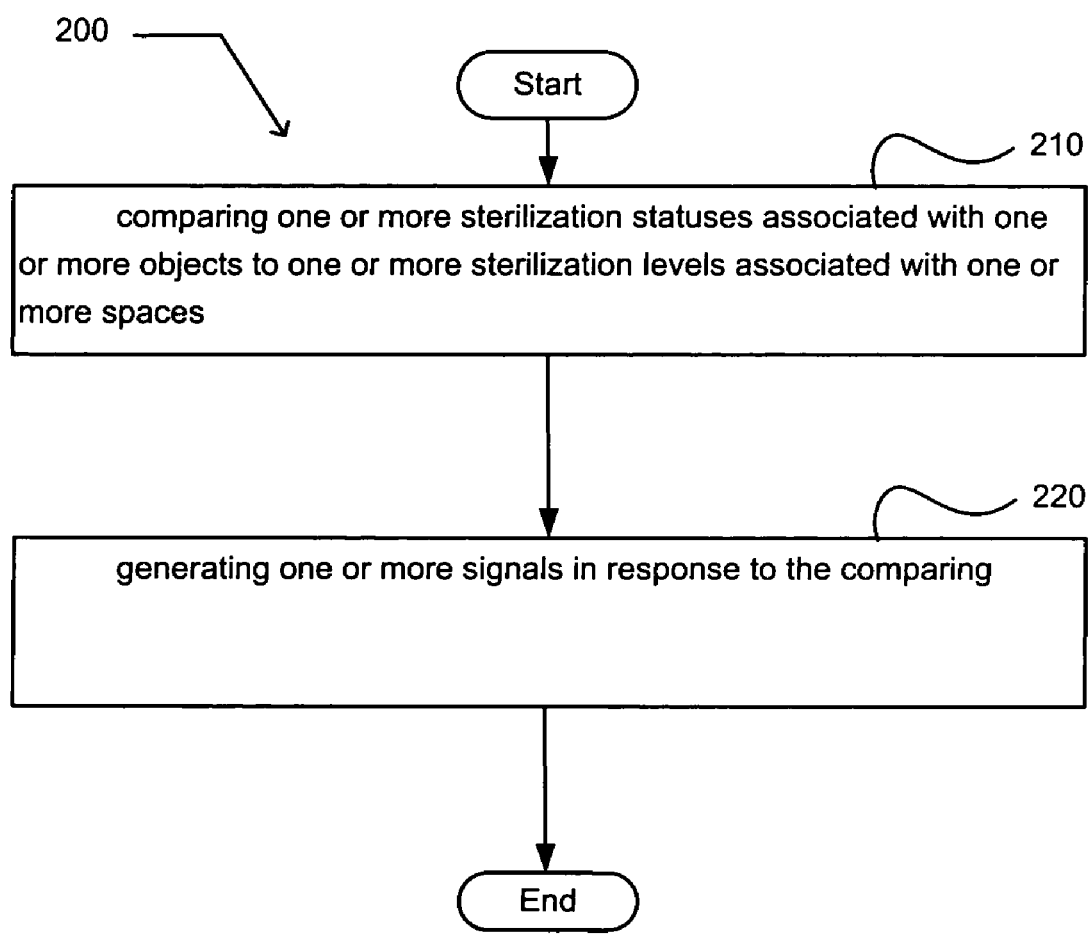
FIG. 2 illustrates an operational flow representing example operations related to monitoring methods.

FIG. 2 illustrates an operational flow 200 representing examples of operations that are related to the performance of a monitoring method. In FIG. 2 and in following figures that include various examples of operations used during performance of the monitoring method, discussion and explanation may be provided with respect to the above-described example of FIG. 1, and/or with respect to other examples and contexts. However, it should be understood that the operations may be executed in a number of other environments and contexts, and/or modified versions of FIG. 1. Also, although the various operations are presented in the sequence(s) illustrated, it should be understood that the various operations may be performed in other orders than those which are illustrated, or may be performed concurrently.

After a start operation, the operational flow 200 includes an operation 210 involving comparing one or more sterilization statuses associated with one or more objects to one or more sterilization levels associated with one or more spaces 104. In some embodiments, one or more comparing units 106 compare one or more sterilization statuses 108 associated with one or more objects 102 to one or more sterilization levels 110 associated with one or more spaces 104. In some embodiments, one or more comparing units 106 compare one sterilization status 108 to one sterilization level 110. In some embodiments, one or more comparing units 106 compare one or more sterilization statuses 108 to one sterilization level 110. In some embodiments, one or more comparing units 106 compare one sterilization status 108 to one or more sterilization levels 110. In some embodiments, one or more comparing units 106 compare one or more values associated with one or more sterilization statuses 108 to one or more values associated with one or more sterilization levels 110. In some embodiments, one or more comparing units 106 compare one or more values associated with one or more sterilization statuses 108 to one or more ranges of values associated with one or more sterilization levels 110. In some embodiments, comparing includes determining if one or more values associated with one or more sterilization statuses 108 are equal to one or more values associated with one or more sterilization levels 110. In some embodiments, comparing includes determining if one or more values associated with one or more sterilization statuses 108 are greater than one or more values associated with one or more sterilization levels 110. In some embodiments, comparing includes determining if one or more values associated with one or more sterilization statuses 108 are less than one or more values associated with one or more sterilization levels 110. In some embodiments, one or more sterilization statuses 108 associated with one or more objects 102 can be designated as being sterile or non-sterile. In some embodiments, one or more sterilization statuses 108 associated with one or more objects 102 can be designated as being sterile for one or more types of contamination and non-sterile for one or more other types of contamination. Accordingly, one or more comparing units 106 can compare one or more sterilization statuses 108 with one or more sterilization levels 110 with regard to one or more types of contamination. In some embodiments, comparing includes determining if one or more values associated with one or more sterilization statuses 108 are within one or more ranges of values associated with one or more sterilization levels 110. In some embodiments, comparing includes determining if one or more values associated with one or more sterilization statuses 108 are outside of one or more ranges of values associated with one or more sterilization levels 110. In some embodiments, one or more sterilization statuses 108 may be associated with one or more objects 102 according to one or more sterilization methods that were used to sterilize the one or more objects 102. In some embodiments, one or more sterilization statuses 108 may be associated with one or more objects 102 according to when the one or more objects 102 were last sterilized. In some embodiments, one or more sterilization statuses 108 may be associated with one or more objects 102 according to a standard, such as those put forth by the International Standards Organization. Accordingly, numerous methods may be used to associate one or more sterilization statuses 108 with one or more objects 102. In some embodiments, one or more sterilization levels 110 may be associated with one or more spaces 104 according a level of sterility desired for the one or more spaces 104. For example, an operating room in a hospital may be associated with a higher sterilization level 110 than a waiting room in a hospital. Accordingly, numerous methods and criteria may be used to associate one or more sterilization levels 110 with one or more spaces 104.

The operational flow 200 also includes a transmitting operation 220 involving generating one or more signals in response to the comparing. In some embodiments, one or more comparing units 106 may generate one or more signals 112 in response to comparing one or more sterilization statuses 108 associated with one or more objects 102 to one or more sterilization levels 110 associated with one or more spaces 104. In some embodiments, the one or more signals 112 are received by one or more recording units 116. In some embodiments, the one or more signals 112 are received by one or more receiving units 114. In some embodiments, the one or more signals 112 are received by one or more recording units 116 and one or more receiving units 114.

Figure 3:
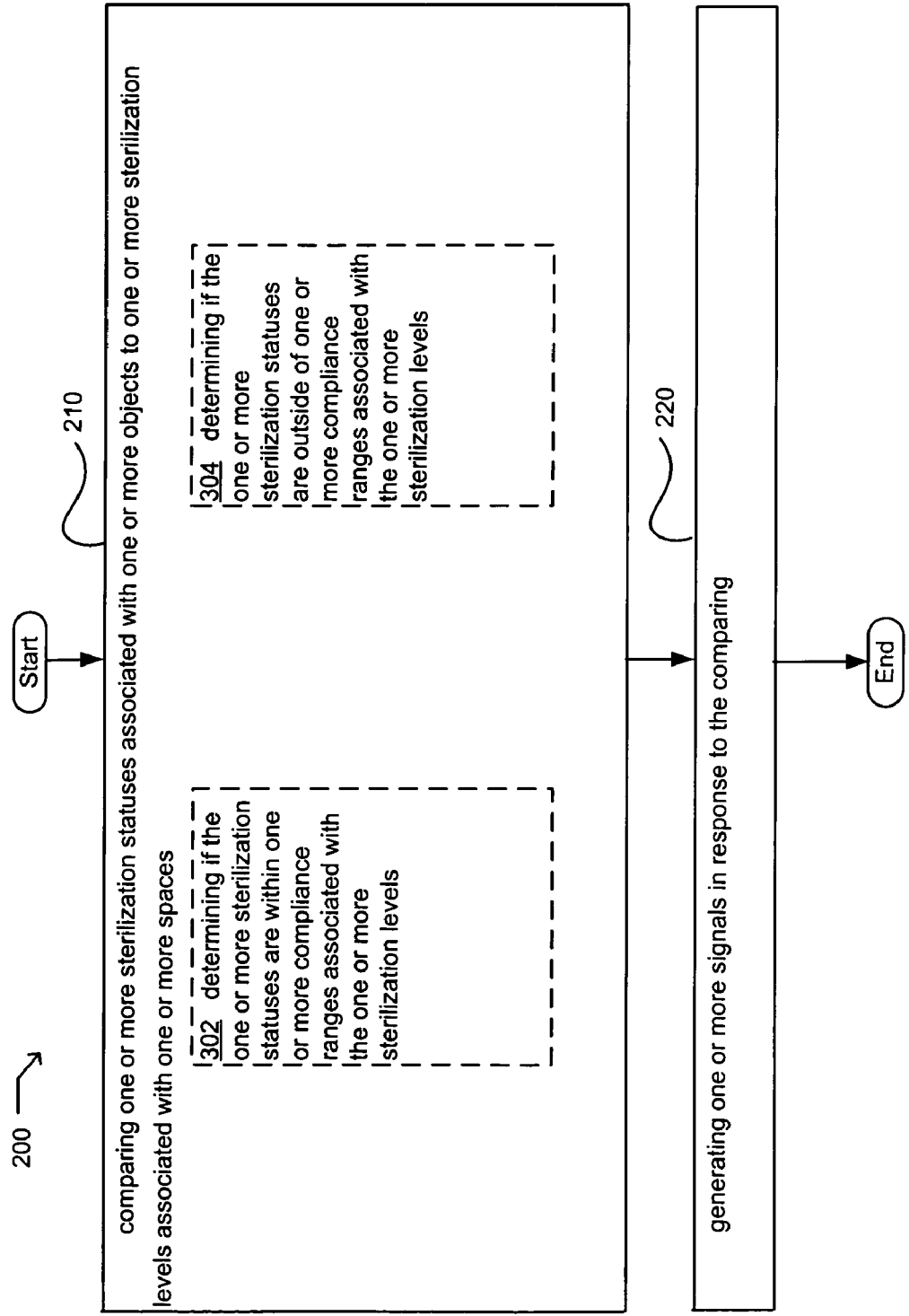
FIG. 3 illustrates an alternative embodiment of the example operation flow of FIG. 2.

FIG. 3 illustrates alternative embodiments of the example operational flow 200 of FIG. 2. FIG. 3 illustrates example embodiments where the comparing operation 210 may include at least one additional operation. Additional operations may include an operation 302 and/or operation 304.

At operation 302, the comparing operation 210 may include determining if one or more sterilization statuses 108 are within one or more compliance ranges associated with one or more sterilization levels 110. In some embodiments, one or more comparing units 106 may determine if one or more sterilization statuses 108 are within one or more compliance ranges associated with one or more sterilization levels 110. In some embodiments, one or more compliance ranges may be associated with one or more sterilization levels 110 according to the level of sterility desired for one or more spaces 104. For example, in some embodiments, one or more spaces 104, such as a hospital examination room that includes a human, may be associated with a medium sterilization level 110 that allows entry of an object 102, such as a human, into the space 104 if the object 102 is associated with a medium or higher sterilization status 108. However, in some embodiments, one or more spaces 104, such as in a hospital operating room where a surgery is to take place, may be associated with a high sterilization level 110 that allows entry of an object 102, such as a human or a surgical instrument, into the space 104 if the object 102 is associated with a high sterilization status 108. Accordingly, one or more sterilization levels 110 associated with one or more spaces 104 can be selected based on the level of sterility desired for the one or more spaces 104. In some embodiments, a sterilization level 110 may include a range of values that may be satisfied by one or more sterilization statuses 108 associated with one or more objects 102. Accordingly, one or more comparing units 106 can compare one or more sterilization statuses 108 with a range of values associated with one or more sterilization levels 110 to determine if the one or more sterilization statuses 108 associated with one or more objects 102 comply with one or more sterilization levels 110 associated with one or more spaces 104.

At operation 304, the comparing operation 210 may include determining if one or more sterilization statuses 108 are outside of one or more compliance ranges associated with one or more sterilization levels 110. In some embodiments, one or more comparing units 106 may determine if one or more sterilization statuses 108 are outside of one or more compliance ranges associated with one or more sterilization levels 110. In some embodiments, one or more compliance ranges may be associated with one or more sterilization levels 110 according to the level of sterility desired for one or more spaces 104. For example, in some embodiments, one or more spaces 104, such as a hospital examination room that includes a human, may be associated with a medium sterilization level 110 that allows entry of an object 102, such as a human, into the space 104 if the object 102 is associated with a medium or higher sterilization status 108. However, in some embodiments, one or more spaces 104, such as in a hospital operating room where a surgery is to take place, may be associated with a high sterilization level 110 that allows entry of an object 102, such as a human or a surgical instrument, into the space 104 if the object 102 is associated with a high sterilization status 108. Accordingly, one or more sterilization levels 110 associated with one or more spaces 104 can be selected based on the level of sterility desired for the one or more spaces 104. In some embodiments, a sterilization level 110 may include a range of values that may be satisfied by one or more sterilization statuses 108 associated with one or more objects 102. Accordingly, one or more comparing units 106 can compare one or more sterilization statuses 108 with a range of values associated with one or more sterilization levels 110 to determine if the one or more sterilization statuses 108 associated with the one or more objects 102 does not comply with the one or more sterilization levels 110 associated with one or more spaces 104.

Figure 4:
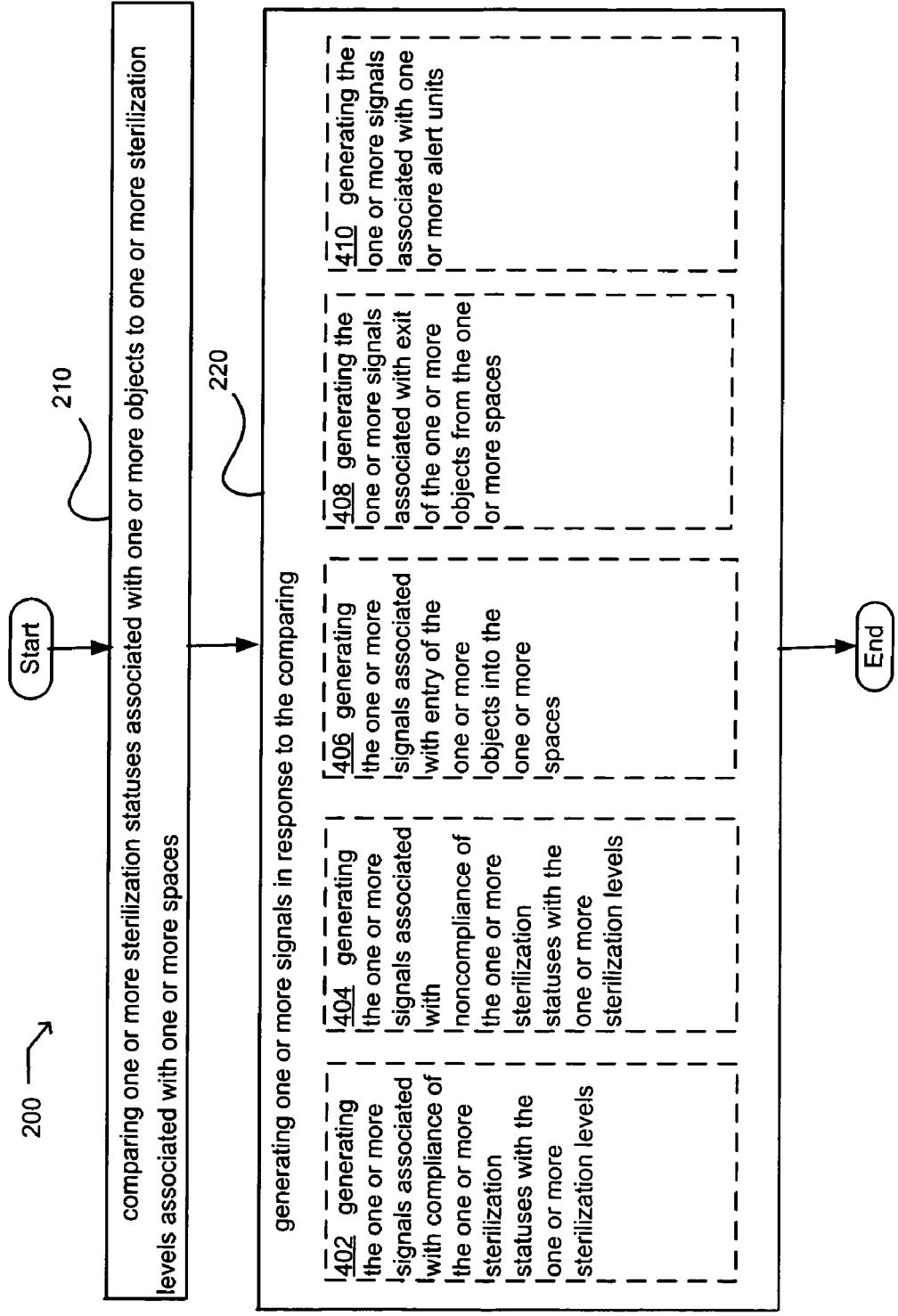
FIG. 4 illustrates an alternative embodiment of the example operation flow of FIG. 2.

FIG. 4 illustrates alternative embodiments of the example operational flow 200 of FIG. 2. FIG. 4 illustrates example embodiments where the generating operation 220 may include at least one additional operation. Additional operations may include an operation 402, 404, 406, 408 and/or operation 410.

At operation 402, the generating operation 220 may include generating one or more signals 112 associated with compliance of one or more sterilization statuses 108 with one or more sterilization levels 110. In some embodiments, one or more comparing units 106 can generate one or more signals 112 associated with compliance of one or more sterilization statuses 108 with one or more sterilization levels 110. In some embodiments, one or more signals 112 are associated with one or more sterilization statuses 108 having associated values that are greater than one or more values associated with one or more sterilization levels 110. Accordingly, one or more comparing units 106 can generate one or more signals indicating that the one or more sterilization statuses 108 associated with the one or more objects 102 meet and/or exceed one or more sterilization levels 110 associated with one or more spaces 104. In some embodiments, one or more signals 112 are associated with one or more sterilization statuses 108 that are within a range of values associated with one or more sterilization levels 110. Accordingly, one or more comparing units 106 may generate one or more signals 112 indicating that the one or more sterilization statuses 108 meet and/or exceed one or more sterilization levels 110 associated with one or more spaces 104. In some embodiments, such signals 112 will allow the one or more objects 102 to enter into the one or more spaces 104. In some embodiments, such signals 112 will allow the one or more objects 102 to exit from the one or more spaces 104. In some embodiments, such signals 112 may be recorded by one or more recording units 116 to record compliance with one or more sterilization levels 110 or one or more sterilization protocols.

At operation 404, the generating operation 220 may include generating one or more signals 112 associated with noncompliance of one or more sterilization statuses 108 with one or more sterilization levels 110. In some embodiments, one or more comparing units 106 can generate one or more signals 112 associated with noncompliance of one or more sterilization statuses 108 with one or more sterilization levels 110. In some embodiments, one or more signals 112 are associated with one or more sterilization statuses 108 that do not meet and/or exceed one or more values associated with one or more sterilization levels 110. Accordingly, one or more comparing units 106 can generate one or more signals 112 indicating that the one or more sterilization statuses 108 associated with the one or more objects 102 do not meet and/or exceed the one or more sterilization levels 110 associated with one or more spaces 104. In some embodiments, one or more signals 112 are associated with one or more sterilization statuses 108 that are not within a range of values associated with one or more sterilization levels 110. Accordingly, one or more comparing units 106 can generate one or more signals 112 indicating that the one or more sterilization statuses 108 do not meet and/or exceed one or more ranges of sterilization levels 110 associated with one or more spaces 104. In some embodiments, such signals 112 will disallow the one or more objects 102 from entering into the one or more spaces 104. In some embodiments, such signals 112 will disallow the one or more objects 102 from exiting from one or more spaces 104. In some embodiments, such signals 112 may be recorded by one or more recording units 116 to record noncompliance with one or more sterilization levels 110 or one or more sterilization protocols.

At operation 406, the generating operation 220 may include generating one or more signals 112 associated with entry of one or more objects 102 into one or more spaces 104. In some embodiments, one or more comparing units 106 can generate one or more signals 112 associated with entry of one or more objects 102 into one or more spaces 104. In some embodiments, one or more comparing units 106 may generate one or more signals 112 associated with entry of one or more objects 102 into one or more spaces 104 after one or more comparing units 106 determine that one or more sterilization statuses 108 associated with one or more objects 102 meet and/or exceed one or more sterilization levels 110 associated with the one or more spaces 104. In some embodiments, one or more comparing units 106 may generate one or more signals 112 associated with entry of one or more objects 102 into one or more spaces 104 after one or more comparing units 106 determine that one or more sterilization statuses 108 associated with one or more objects 102 are within a range of values associates with one or more sterilization levels 110 associated with the one or more spaces 104. In some embodiments, one or more comparing units 106 may generate one or more signals 112 associated with disallowing entry of one or more objects 102 into one or more spaces 104 after one or more comparing units 106 determine that one or more sterilization statuses 108 associated with the one or more objects 102 do not meet and/or exceed one or more sterilization levels 110 associated with the one or more spaces 104. In some embodiments, one or more comparing units 106 may generate one or more signals 112 associated with disallowing entry of one or more objects 102 into one or more spaces 104 after one or more comparing units 106 determine that one or more sterilization statuses 108 associated with one or more objects 102 are not within a range of values associated with one or more sterilization levels 110 that are associated with the one or more spaces 104. Accordingly, in some embodiments, such a generating operation 220 may be used to allow one or more sterile objects 102, or one or more objects 102 having high sterilization status 108, entry into one or more spaces 104 that are sterile or that are associated with a high sterility level I 10. In other embodiments, such a generating operation 220 may be used to prohibit one or more non-sterile objects 102, or one or more objects 102 having low sterilization status 108, from entry into one or more spaces 104 that are sterile or that are associated with a high sterility level 110.

At operation 408, the generating operation 220 may include generating one or more signals 112 associated with exit of one or more objects 102 from one or more spaces 104. In some embodiments, one or more comparing units 106 can generate one or more signals 112 associated with exit of one or more objects 102 from one or more spaces 104. In some embodiments, one or more comparing units 106 may generate one or more signals 112 associated with exit of one or more objects 102 from one or more spaces 104 after one or more comparing units 106 determine that one or more sterilization statuses 108 associated with the one or more objects 102 meet and/or exceed one or more sterilization levels 110 associated with one or more spaces 104. In some embodiments, one or more comparing units 106 may generate one or more signals 112 associated with disallowing exit of one or more objects 102 from one or more spaces 104 after one or more comparing units 106 determine that one or more sterilization statuses 108 associated with one or more objects 102 do not meet and/or exceed one or more sterilization levels 110 associated with one or more spaces 104. Accordingly, in some embodiments, such a generating operation 220 may be used to allow one or more sterile objects 102, or one or more objects 102 having high sterilization status 108, to exit from one or more spaces 104 that are sterile or that are associated with a high sterility level 110. In other embodiments, such a generating operation 220 may be used to prohibit one or more non-sterile objects 102, or one or more objects 102 having low sterilization status 108, from exiting one or more spaces 104 that are non-sterile or that are associated with a low sterility level 110.

At operation 410, the generating operation 220 may include generating one or more signals 112 associated with one or more alert units 128. In some embodiments, one or more comparing units 106 can generate one or more signals 112 associated with one or more alert units 128. In some embodiments, one or more comparing units 106 may generate one or more signals 112 associated with one or more alert units 128 after one or more comparing units 106 determine that one or more values associated with one or more sterilization statuses 108 associated with one or more objects 102 meet and/or exceed one or more values associated with one or more sterilization levels 110 associated with one or more spaces 104. For example, in some embodiments, a space 104 surrounding a patient in a hospital may be associated with a medium sterilization level 110. An object 102, such as a physician, that is associated with a medium or higher sterilization status 108 may enter into the space 104 surrounding the patient without causing one or more alert units 128 to indicate noncompliance of the object 102 with the space 104. For example, one or more alert units 128 may refrain from sounding an alarm, flashing a red light, or other such indicator. In some embodiments, an object 102, such as a physician, that is associated with a medium or higher sterilization status 108 may enter into the space 104 surrounding the patient and cause one or more alert units 128 to indicate compliance of the object 102 with the space 104. For example, one or more alert units 128 may flash a green light, activate a voice recording indicating compliance, or other such indicator. In some embodiments, one or more comparing units 106 may generate one or more signals 112 associated with one or more alert units 128 after the one or more comparing units 106 determine that one or more values associated with one or more sterilization statuses 108 associated with the one or more objects 102 do not meet and/or exceed one or more values associated with one or more sterilization levels 110 associated with one or more spaces 104. For example, in some embodiments, a space 104 surrounding a patient in a hospital may be associated with a medium or higher sterilization level 110. Entry of an object 102, such as a physician, that is associated with a low sterilization status 108 into the space 104 surrounding the patient may cause one or more alert units 128 to indicate noncompliance of the object 102 with the space 104. For example, one or more alert units 128 may sound an alarm, flash a red light, or other such indicator.

Figure 5:
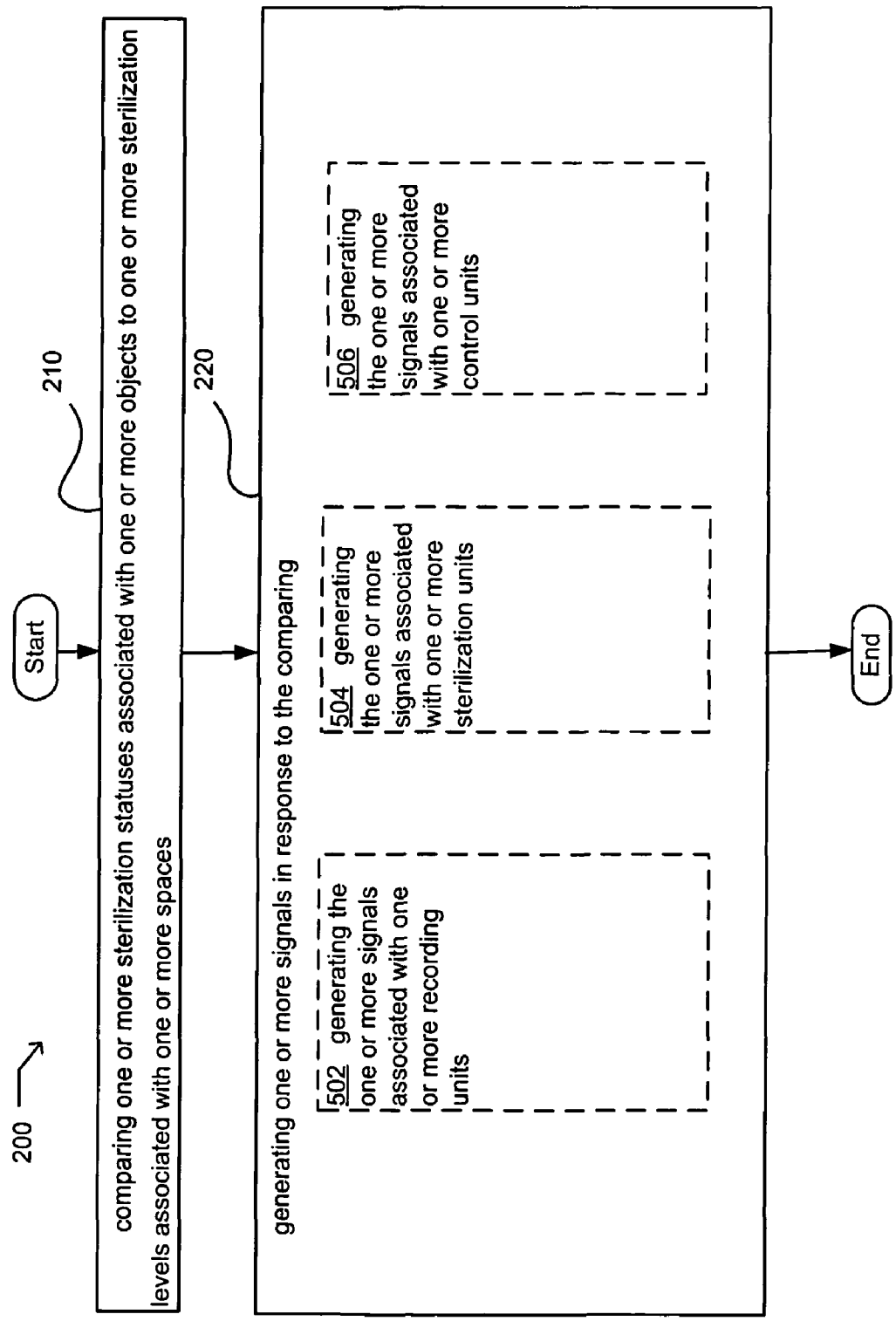
FIG. 5 illustrates an alternative embodiment of the example operation flow of FIG. 2.

FIG. 5 illustrates alternative embodiments of the example operational flow 200 of FIG. 2. FIG. 5 illustrates example embodiments where the generating operation 220 may include at least one additional operation. Additional operations may include an operation 502, 504 and/or operation 506.

At operation 502, the generating operation 220 may include generating one or more signals 112 associated with one or more recording units 116. In some embodiments, one or more comparing units 106 can generate one or more signals 112 associated with one or more recording units 116. In some embodiments, one or more signals 112 may be generated that indicate one or more positions of one or more objects 102 about one or more spaces 104. In some embodiments, such signals 112 may be generated by one or more comparing units 106. In some embodiments, one or more signals 112 may be recorded by one or more recording units 116. For example, in some embodiments, the positions of one or more surgical instruments may be tracked as they are moved about one or more spaces 104 in a hospital. In addition, one or more signals 112 indicating the sterilization status 108 of one or more objects 102 may be generated. In some embodiments, such signals 112 may be generated by one or more comparing units 106. In some embodiments, these one or more signals 112 may be recorded by one or more recording units 116. For example, in some embodiments, one or more signals 112 associated with one or more sterilization statuses 108 associated with one or more surgical instruments can be recorded by one or more recording units 116. Accordingly, one or more sterilization statuses 108 associated with one or more objects 102 can be tracked over time and recorded by one or more recording units 116. In some embodiments, one or more signals 112 indicating the position and sterilization status 108 of one or more objects 102 about one or more spaces 104 can be generated. Such signals 112 can be recorded by one or more recording units 116. In some embodiments, such recorded signals 112 may be used to monitor and/or report compliance or noncompliance with one or more protocols associated with one or more spaces 104. For example, a hospital may have an established protocol with regard to sterilization procedures used to sterilize surgical instruments. Records indicating when and where the surgical instruments were sterilized and where the instruments were transported may establish adherence to a sterilization protocol.

At operation 504, the generating operation 220 may include generating one or more signals associated with one or more sterilization units. In some embodiments, one or more comparing units 106 can generate one or more signals 112 associated with one or more sterilization units 126. In some embodiments, one or more signals 112 may be generated that instruct one or more sterilization units 126 to sterilize one or more objects 102. For example, in some embodiments, one or more signals 112 may be generated that indicate that one or more objects 102 are associated with one or more low sterilization statuses 108 and should be sterilized. Accordingly, one or more signals 112 may be received by one or more sterilization units 126 that will act to sterilize one or more objects 102. In some embodiments, one or more signals 112 may be generated that indicate that one or more objects 102 are associated with one or more high sterilization statuses 108 and should not be sterilized. Accordingly, one or more signals 112 may be received by one or more sterilization units 126 that will then refrain from sterilizing one or more objects 102. In some embodiments, one or more comparing units 106 can change the sterilization status 108 of one or more objects 102. For example, in some embodiments, one or more comparing units 106 can change the sterilization status 108 of one or more non-sterile objects 102 to sterile after the one or more objects 102 have been sterilized. In some embodiments, one or more sterilization units 126 can change the sterilization status 108 of one or more objects 102. For example, in some embodiments, one or more sterilization units 126 can change the sterilization status 108 of one or more non-sterile objects 102 to sterile after the one or more objects 102 have been sterilized. For example, in some embodiments, a physician may initially be associated with a medium or higher sterilization status 108 upon entering into a first space 104 that is associated with a medium sterilization level 110 and that includes a first patient. Upon leaving the first space 104 after examining the first patient, one or more comparing units 106 may change the sterilization status 108 associated with the physician to a low sterilization status 108. In some embodiments, the physician now associated with low sterilization status 108 after examining the first patient may be prohibited from entering into a second space 104 that is associated with a medium sterilization level 110 and that includes a second patient. One or more comparing units 106 may generate one or more signals 112 indicating that one or more sterilization agents need to be applied to the physician. Accordingly, one or more sterilization units 126 may be utilized to apply one or more sterilization agents to the physician. Upon completion of one or more sterilization procedures, the sterilization status 108 associated with the physician may be changed to a medium or higher sterilization status 108. In some embodiments, the sterilization status 108 associated with the physician may be changed by one or more comparing units 106, by one or more sterilization units 126, and/or substantially any combination thereof. The physician may now be allowed entry into the second space 104 as the physician is now associated with a medium or higher sterilization status 108. Such methods may be utilized with numerous objects 102.

At operation 506, the generating operation 220 may include generating one or more signals 112 associated with one or more control units 130. In some embodiments, one or more comparing units 106 can generate one or more signals 112 associated with one or more control units 130. Control units 130 may be configured in numerous ways. Examples of ways in which a control unit 130 may be configured include, but are not limited to, locks, doors, lights, switches, internet connections, transmitters, receivers, and the like. In some embodiments, one or more control signals 120 may be generated that are associated with one or more control units 130 that may be configured as part of a lock or a door. Accordingly, the one or more control signals 120 may control entry or exit from one or more spaces 104 having entry or exit that is controlled by such a lock or door. In some embodiments, one or more control units 130 may be configured as a switch.

After a start operation, the operational flow 600 includes a receiving operation 610 involving receiving one or more signals generated in response to comparing one or more sterilization statuses associated with one or more objects to one or more sterilization levels associated with one or more spaces 104. In some embodiments, one or more receiving units 114 may receive one or more signals 112 generated in response to comparing one or more sterilization statuses 108 associated with one or more objects 102 to one or more sterilization levels 110 associated with one or more spaces 104.

The operational flow 600 also includes a responding operation 620 involving responding to the receiving. In some embodiments, one or more responding units 118 generate one or more control signals 120 associated with receiving one or more signals 112 generated in response to comparing one or more sterilization statuses 108 associated with one or more objects 102 to one or more sterilization levels 110 associated with one or more spaces 104.

Figure 6:
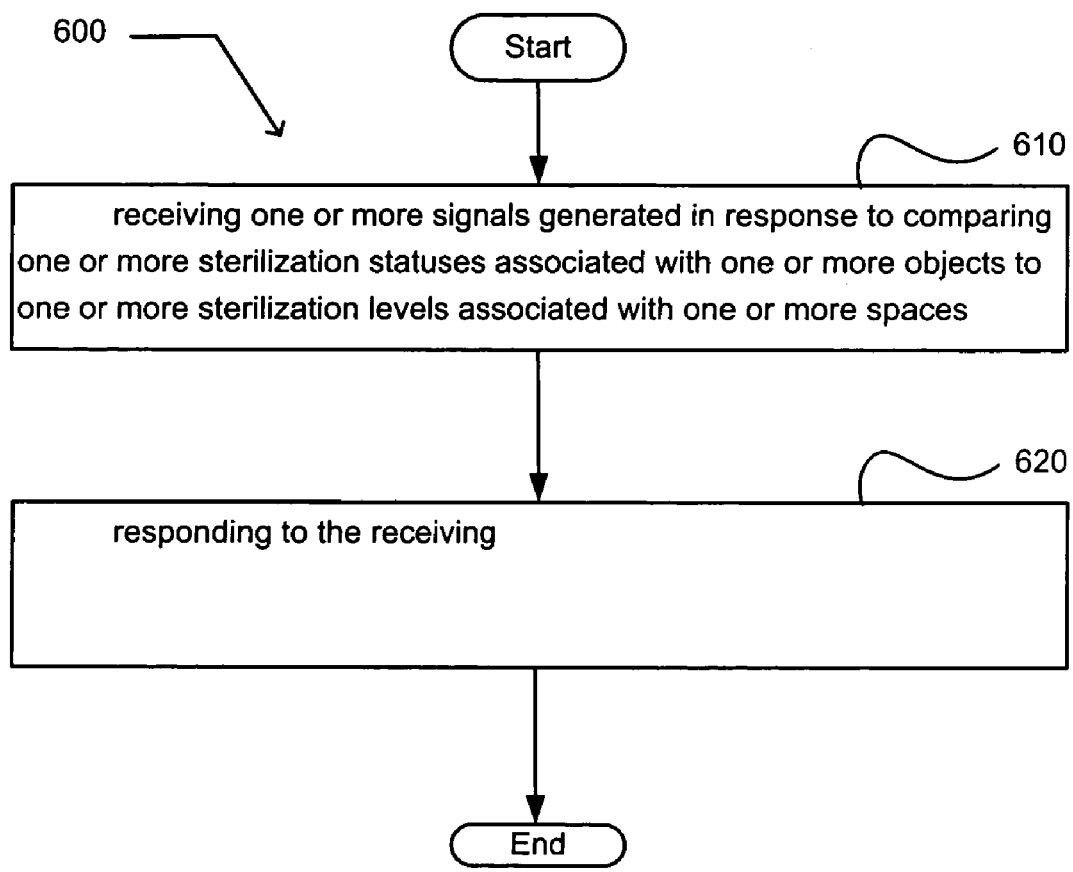
FIG. 6 illustrates an operational flow representing example operations related to monitoring methods.
Figure 7:
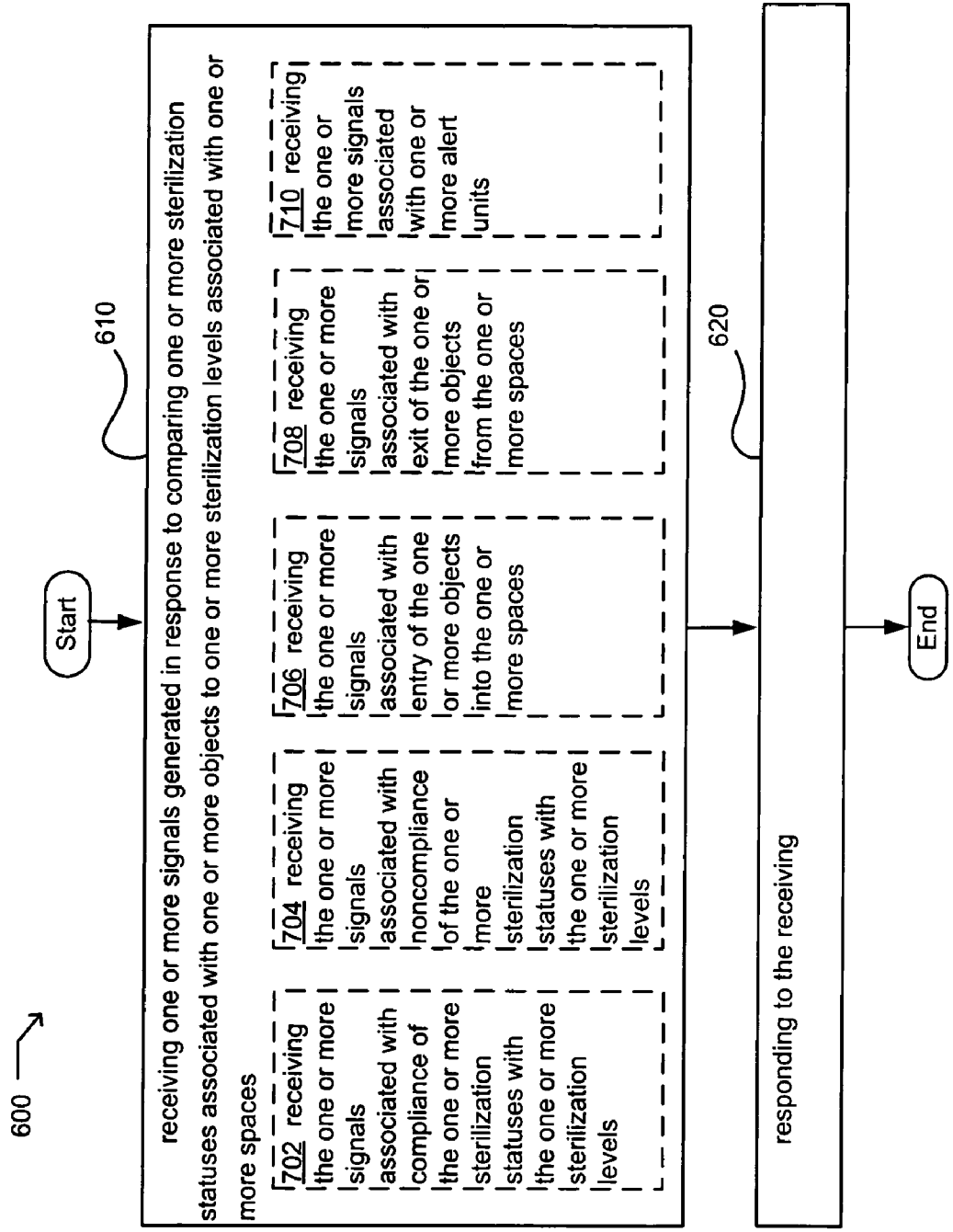
FIG. 7 illustrates an alternative embodiment of the example operation flow of FIG. 6.

FIG. 7 illustrates alternative embodiments of the example operational flow 600 of FIG. 6. FIG. 7 illustrates example embodiments where the receiving operation 610 may include at least one additional operation. Additional operations may include an operation 702, 704, 706, 708 and/or operation 710.

At operation 702, the receiving operation 610 may include receiving one or more signals 112 associated with compliance of one or more sterilization statuses 108 with one or more sterilization levels 110. In some embodiments, one or more receiving units 114 receive one or more signals 112 associated with compliance of one or more sterilization statuses 108 with one or more sterilization levels 110. In some embodiments, one or more signals 112 are associated with one or more sterilization statuses 108 having associated values that are greater than one or more values associated with one or more sterilization levels 110. Accordingly, in some embodiments, one or more receiving units 114 can receive one or more signals indicating that one or more sterilization statuses 108 associated with the one or more objects 102 meet and/or exceed one or more sterilization levels 110 associated with one or more spaces 104. In some embodiments, one or more signals 112 are associated with one or more sterilization statuses 108 that are within a range of values associated with one or more sterilization levels 110. Accordingly, one or more receiving units 114 can receive one or more signals 112 indicating that the one or more sterilization statuses 108 meet and/or exceed the one or more sterilization levels 110 associated with one or more spaces 104. In some embodiments, such signals 112 will allow the one or more objects 102 to enter into the one or more spaces 104. In some embodiments, such signals 112 will be recorded by one or more recording units 116 to record compliance with one or more sterilization levels 110 or one or more sterilization protocols.

At operation 704, the receiving operation 610 may include receiving one or more signals associated with noncompliance of one or more sterilization statuses with one or more sterilization levels. In some embodiments, one or more receiving units 114 can receive one or more signals 112 associated with noncompliance of one or more sterilization statuses 108 with one or more sterilization levels 110. In some embodiments, one or more signals 112 are associated with one or more sterilization statuses 108 that do not meet and/or exceed one or more values associated with one or more sterilization levels 110. Accordingly, one or more receiving units 114 can receive one or more signals indicating that the one or more sterilization statuses 108 associated with the one or more objects 102 do not meet and/or exceed the one or more sterilization levels 110 associated with one or more spaces 104. In some embodiments, one or more signals 112 are associated with one or more sterilization statuses 108 that are not within a range of values associated with one or more sterilization levels 110. Accordingly, one or more receiving units 114 can receive one or more signals 112 indicating that the one or more sterilization statuses 108 do not meet and/or exceed one or more ranges of sterilization levels 110 associated with one or more spaces 104. In some embodiments, such signals 112 will disallow the one or more objects 102 from entering into the one or more spaces 104. In some embodiments, such signals 112 will be recorded by one or more recording units 116 to record noncompliance with one or more sterilization levels 110 or one or more sterilization protocols.

At operation 706, the receiving operation 610 may include receiving one or more signals associated with entry of one or more objects into one or more spaces. In some embodiments, one or more receiving units 114 can receive one or more signals 112 associated with entry of one or more objects 102 into one or more spaces 104. In some embodiments, one or more receiving units 114 may receive one or more signals 112 associated with entry of one or more objects 102 into one or more spaces 104 from one or more comparing units 106 which determined that the one or more sterilization statuses 108 associated with the one or more objects 102 meet and/or exceed one or more sterilization levels 110 associated with the one or more spaces 104. In some embodiments, one or more receiving units 114 may receive one or more signals 112 associated with entry of one or more objects 102 into one or more spaces 104 from one or more comparing units 106 which determines that the one or more sterilization statuses 108 associated with the one or more objects 102 are within a range of values associated with one or more sterilization levels 110 that are associated with the one or more spaces 104. In some embodiments, one or more receiving units 114 may receive one or more signals 112 associated with disallowing entry of one or more objects 102 into one or more spaces 104 from one or more comparing units 106 which determined that the one or more sterilization statuses 108 associated with the one or more objects 102 do not meet and/or exceed one or more sterilization levels 110 associated with the one or more spaces 104. In some embodiments, one or more receiving units 114 may receive one or more signals 112 associated with disallowing entry of one or more objects 102 into one or more spaces 104 from one or more comparing units 106 which determined that the one or more sterilization statuses 108 associated with the one or more objects 102 are not within a range of values associated with one or more sterilization levels 110 that are associated with the one or more spaces 104. Accordingly, in some embodiments, such a receiving operation 610 may be used to allow one or more sterile objects 102, or one or more objects 102 having high sterilization status 108, entry into one or more spaces 104 that are sterile or that are associated with a high sterility level 110. In other embodiments, such a receiving operation 610 may be used to prohibit one or more non-sterile objects 102, or one or more objects 102 having low sterilization status 108, from entry into one or more spaces 104 that are sterile or that are associated with a high sterility level 110.

At operation 708, the receiving operation 610 may include receiving one or more signals 112 associated with exit of one or more objects 102 from one or more spaces 104. In some embodiments, one or more receiving units 114 can receive one or more signals 112 associated with exit of one or more objects 102 from one or more spaces 104. In some embodiments, one or more receiving units 114 may receive one or more signals 112 associated with exit of one or more objects 102 from one or more spaces 104 from one or more comparing units 106 which determine that the one or more sterilization statuses 108 associated with the one or more objects 102 meet and/or exceed one or more sterilization levels 110 associated with one or more spaces 104. In some embodiments, one or more receiving units 114 may receive one or more signals 112 associated with disallowing exit of one or more objects 102 from one or more spaces 104 from one or more comparing units 106 which determined that one or more sterilization statuses 108 associated with the one or more objects 102 do not meet and/or exceed one or more sterilization levels 110 associated with one or more spaces 104. Accordingly, in some embodiments, such a receiving operation 610 may be used to allow one or more sterile objects 102, or one or more objects 102 having high sterilization status 108, to exit from one or more spaces 104 that are sterile or that are associated with a high sterility level 110. In other embodiments, such a receiving operation 610 may be used to prohibit one or more non-sterile objects 102, or one or more objects 102 having low sterilization status 108, from exiting one or more spaces 104 that are non-sterile or that are associated with a low sterility level 110.

At operation 710, the receiving operation 610 may include receiving one or more signals 112 associated with one or more alert units 128. In some embodiments, one or more receiving units 114 can receive one or more signals 112 associated with one or more alert units 128. In some embodiments, one or more receiving units 114 may receive one or more signals 112 associated with one or more alert units 128 from one or more comparing units 106 which determined that one or more values associated with one or more sterilization statuses 108 associated with the one or more objects 102 meet and/or exceed one or more values associated with one or more sterilization levels 110 associated with one or more spaces 104. For example, in some embodiments, a space 104 surrounding a patient in a hospital may be associated with a medium sterilization level 110. An object 102, such as a physician, that is associated with a medium or higher sterilization status 108 may enter into the space 104 surrounding the patient without causing one or more alert units 128 to indicate noncompliance of the object 102 with the space 104. For example, one or more alert units 128 may refrain from sounding an alarm, flashing a red light, or other such indicator. In some embodiments, an object 102, such as a physician, that is associated with a medium or higher sterilization status 108 may enter into the space 104 surrounding the patient and cause one or more alert units 128 to indicate compliance of the object 102 with the space 104. For example, one or more alert units 128 may flash a green light, activate a voice recording indicating compliance, or other such indicator. In some embodiments, one or more receiving units 114 may receive one or more signals 112 associated with one or more alert units 128 from one or more comparing units 106 which determined that one or more values associated with one or more sterilization statuses 108 associated with the one or more objects 102 are less than a value associated with one or more sterilization levels 110 associated with one or more spaces 104. For example, in some embodiments, a space 104 surrounding a patient in a hospital may be associated with a medium sterilization level 110. An object 102, such as a physician, that is associated with a low sterilization status 108 may enter into the space 104 surrounding the patient and cause one or more alert units 128 to indicate noncompliance of the object 102 with the space 104. For example, one or more alert units 128 may sound an alarm, flash a red light, or other such indicator.

Figure 8:
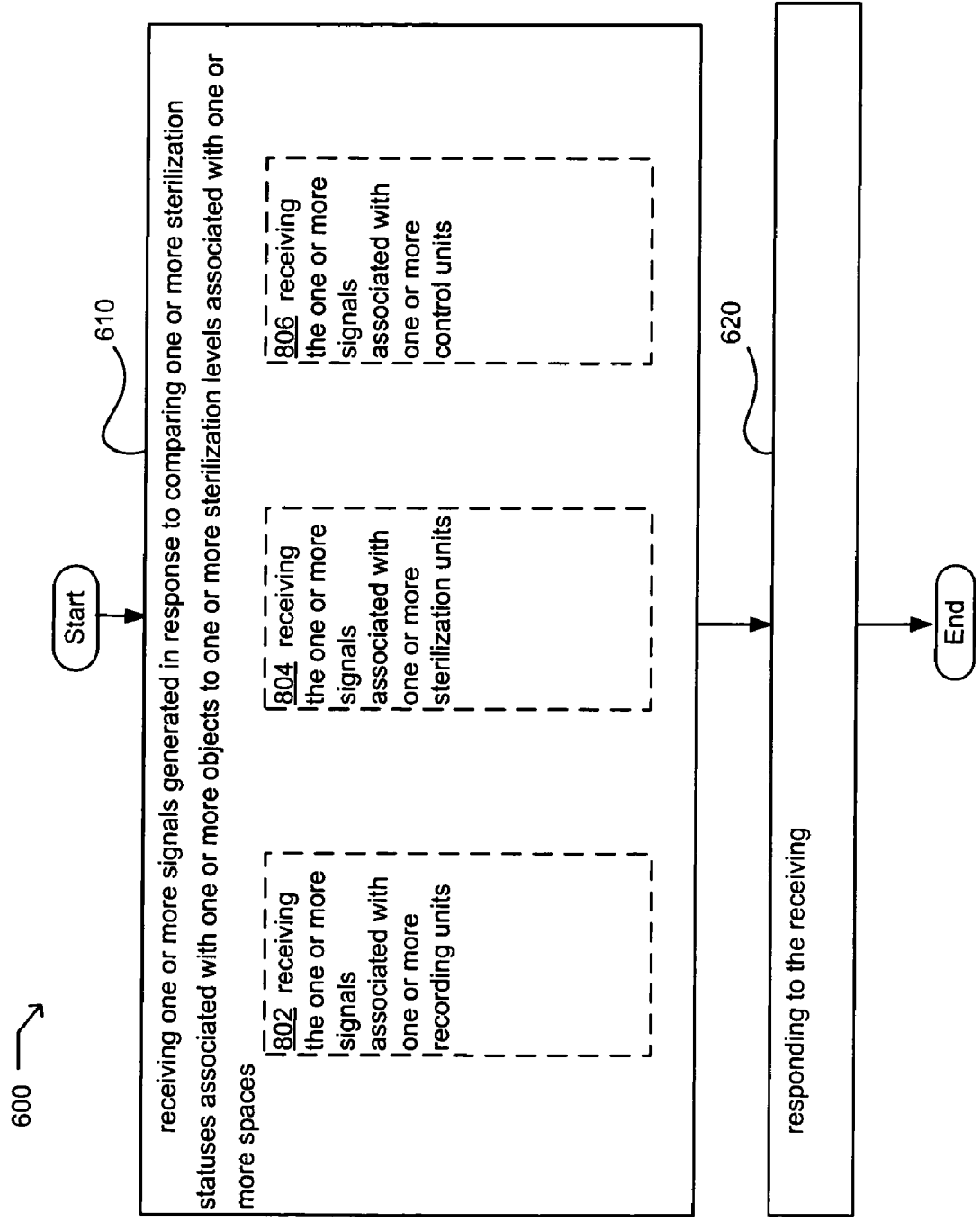
FIG. 8 illustrates an alternative embodiment of the example operation flow of FIG. 6.

FIG. 8 illustrates alternative embodiments of the example operational flow 600 of FIG. 6. FIG. 8 illustrates example embodiments where the receiving operation 610 may include at least one additional operation. Additional operations may include an operation 802, 804 and/or operation 806.

At operation 802, the receiving operation 610 may include receiving one or more signals 112 associated with one or more recording units 116. In some embodiments, one or more receiving units 114 can receive one or more signals 112 associated with one or more recording units 116. In some embodiments, one or more signals 112 may be received that indicate one or more positions of one or more objects 102 about one or more spaces 104. In some embodiments, such signals 112 may be received from one or more comparing units 106. In some embodiments, positions of one or more surgical instruments may be tracked as they are moved about one or more spaces 104 in a hospital. In addition, one or more signals 112 indicating the sterilization status 108 of one or more objects 102 may be received. In some embodiments, such signals 112 may be received by one or more receiving units 114. In some embodiments, these one or more signals 112 may be recorded by one or more recording units 116. For example, in some embodiments, one or more signals 112 associated with one or more sterilization statuses 108 associated with one or more surgical instruments can be received and recorded by one or more recording units 116. Accordingly, one or more sterilization statuses 108 associated with one or more objects 102 can be tracked over time and recorded by one or more recording units 116. In some embodiments, one or more signals 112 indicating the position and sterilization status 108 of one or more objects 102 about one or more spaces 104 can be received. Such signals 112 can be recorded by one or more recording units 116. In some embodiments, such recorded signals 112 may be used to monitor and/or report compliance or noncompliance with one or more protocols associated with one or more spaces 104. For example, a hospital may have an established protocol with regard to sterilization procedures used to sterilize surgical instruments. Records indicating when and where the surgical instruments were sterilized and where the instruments were transported may establish adherence to a sterilization protocol.

At operation 804, the receiving operation 610 may include receiving one or more signals associated with one or more sterilization units. In some embodiments, one or more receiving units 114 can receive one or more signals 112 associated with one or more sterilization units 126. In some embodiments, one or more signals 112 may be received that instruct one or more sterilization units 126 to sterilize one or more objects 102. For example, in some embodiments, one or more signals 112 may be received that indicate that one or more objects 102 are associated with one or more low sterilization statuses 108 and should be sterilized. Accordingly, one or more signals 112 may be received by one or more sterilization units 126 that will act to sterilize one or more objects 102. In some embodiments, one or more signals 112 may be received that indicate that one or more objects 102 are associated with one or more high sterilization statuses 108 and should not be sterilized. Accordingly, one or more signals 112 may be received by one or more sterilization units 126 that will then refrain from sterilizing one or more objects 102.

At operation 806, the receiving operation 610 may include receiving one or more signals associated with one or more control units. In some embodiments, one or more receiving units 114 can receive one or more signals 112 associated with one or more control units 130. Control units 130 may be configured in numerous ways. Examples of ways in which a control unit 130 may be configured include, but are not limited to, locks, doors, lights, switches, internet connections, transmitters, receivers, and the like. In some embodiments, one or more signals 112 may be received that are associated with one or more control units 130 that may be configured as part of a lock or a door. Accordingly, the one or more signals 112 may control entry or exit from one or more spaces 104 having entry or exit that is controlled by such a lock or door. In some embodiments, one or more control units 130 may be configured as a switch.

Figure 9:
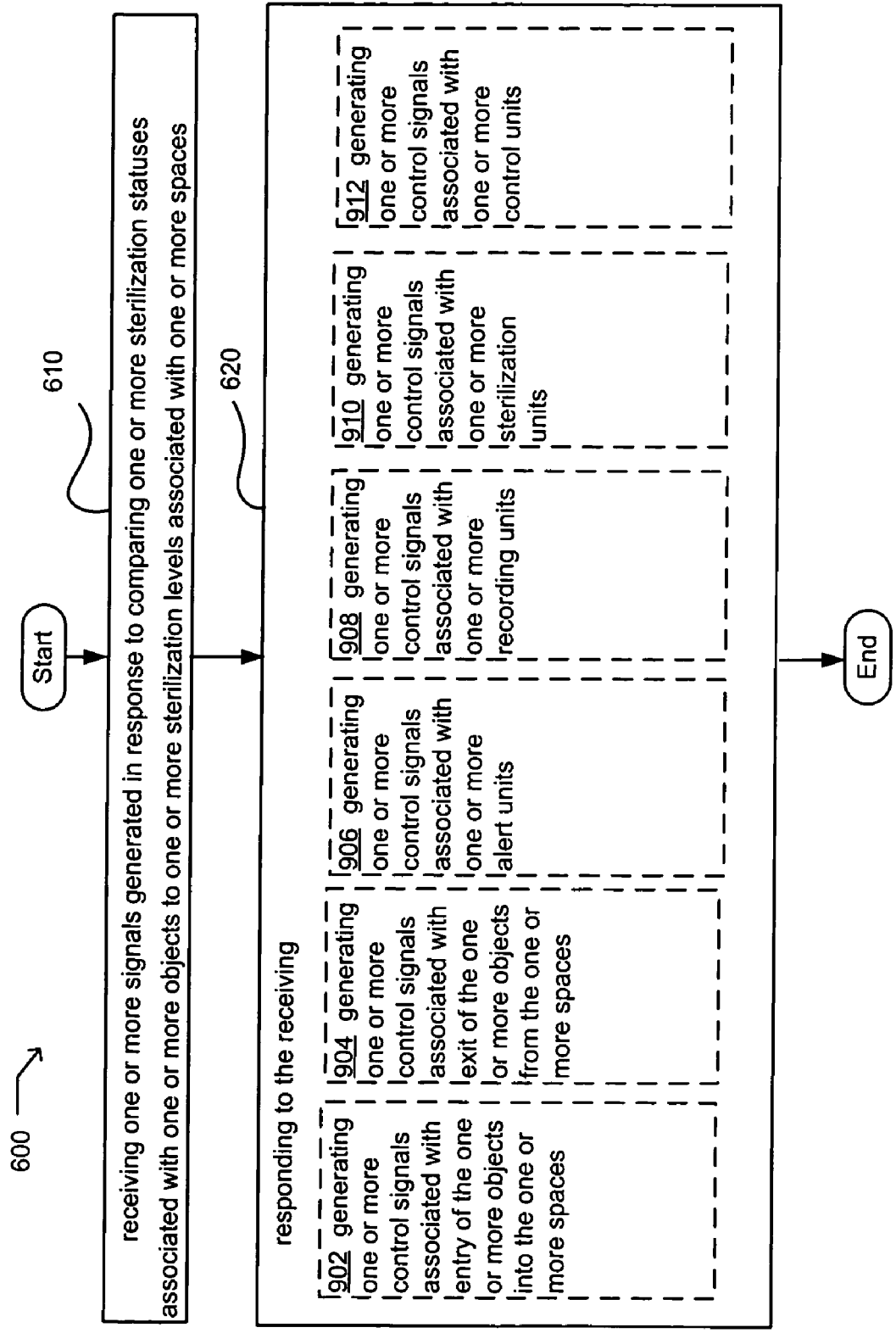
FIG. 9 illustrates an alternative embodiment of the example operation flow of FIG. 6.

FIG. 9 illustrates alternative embodiments of the example operational flow 600 of FIG. 6. FIG. 9 illustrates example embodiments where the responding operation 620 may include at least one additional operation. Additional operations may include an operation 902, 904, 906, 908, 910 and/or operation 912.

At operation 902, the responding operation 620 may include generating one or more control signals 120 associated with entry of one or more objects 102 into one or more spaces 104. In some embodiments, one or more responding units 118 can generate one or more control signals 120 associated with entry of one or more objects 102 into one or more spaces 104. In some embodiments, one or more responding units 118 may generate one or more control signals 120 associated with entry of one or more objects 102 into one or more spaces 104 after one or more comparing units 106 determine that one or more sterilization statuses 108 associated with the one or more objects 102 meet and/or exceed one or more sterilization levels 110 associated with the one or more spaces 104. In some embodiments, one or more responding units 118 may generate one or more control signals 120 associated with entry of one or more objects 102 into one or more spaces 104 after one or more comparing units 106 determine that one or more sterilization statuses 108 associated with the one or more objects 102 are within a range of values associated with one or more sterilization levels 110 associated with the one or more spaces 104. In some embodiments, one or more responding units 118 may generate one or more control signals 120 associated with disallowing entry of one or more objects 102 into one or more spaces 104 after one or more comparing units 106 determine that one or more sterilization statuses 108 associated with the one or more objects 102 do not meet and/or exceed one or more sterilization levels 110 associated with the one or more spaces 104. In some embodiments, one or more responding units 118 may generate one or more control signals 120 associated with disallowing entry of one or more objects 102 into one or more spaces 104 after one or more comparing units 106 determine that the one or more sterilization statuses 108 associated with the one or more objects 102 are not within a range of values associated with one or more sterilization levels 110 that are associated with the one or more spaces 104. Accordingly, in some embodiments, such a responding operation 620 may be used to allow one or more sterile objects 102, or one or more objects 102 having high sterilization status 108, entry into one or more spaces 104 that are sterile or that are associated with a high sterility level 110. In other embodiments, such a responding operation 620 may be used to prohibit one or more non-sterile objects 102, or one or more objects 102 having low sterilization status 108, from entry into one or more spaces 104 that are sterile or that are associated with a high sterility level 110.

At operation 904, the responding operation 620 may include generating one or more control signals 120 associated with exit of one or more objects 102 from one or more spaces 104. In some embodiments, one or more responding units 118 can generate one or more control signals 120 associated with exit of one or more objects 102 from one or more spaces 104. In some embodiments, one or more responding units 118 may generate one or more control signals 120 associated with exit of one or more objects 102 from one or more spaces 104 after one or more comparing units 106 determine that one or more sterilization statuses 108 associated with the one or more objects 102 meet and/or exceed one or more sterilization levels 110 associated with the one or more spaces 104. In some embodiments, one or more responding units 118 may generate one or more control signals 120 associated with disallowing exit of one or more objects 102 from one or more spaces 104 after one or more comparing units 106 determine that one or more sterilization statuses 108 associated with the one or more objects 102 do not meet and/or exceed one or more sterilization levels 110 associated with one or more spaces 104. Accordingly, in some embodiments, such a responding operation 620 may be used to allow one or more sterile objects 102, or one or more objects 102 having high sterilization status 108, to exit from one or more spaces 104 that are sterile or that are associated with a high sterility level 110. In other embodiments, such a responding operation 620 may be used to prohibit one or more non-sterile objects 102, or one or more objects 102 having low sterilization status 108, from exiting one or more spaces 104 that are non-sterile or that are associated with a low sterility level 110.

At operation 906, the responding operation 620 may include generating one or more control signals 120 associated with one or more alert units 128. In some embodiments, one or more responding units 118 can generate one or more control signals 120 associated with one or more alert units 128. In some embodiments, one or more responding units 118 may generate one or more control signals 120 associated with one or more alert units 128 after one or more comparing units 106 determine that one or more values associated with one or more sterilization statuses 108 associated with one or more objects 102 meet and/or exceed one or more values associated with one or more sterilization levels 110 associated with one or more spaces 104. For example, in some embodiments, a space 104 surrounding a patient in a hospital may be associated with a medium sterilization level 110. An object 102, such as a physician, that is associated with a medium or higher sterilization status 108 may enter into the space 104 surrounding the patient without causing one or more alert units 128 to indicate noncompliance of the object 102 with the space 104. For example, one or more alert units 128 may refrain from sounding an alarm, flashing a red light, or other such indicator. In some embodiments, an object 102, such as a physician, that is associated with a medium or higher sterilization status 108 may enter into the space 104 surrounding the patient and cause one or more alert units 128 to indicate compliance of the object 102 with the space 104. For example, one or more alert units 128 may flash a green light, activate a voice recording indicating compliance, or other such indicator. In some embodiments, one or more responding units 118 may generate one or more control signals 120 associated with one or more alert units 128 after one or more comparing units 106 determine that one or more values associated with one or more sterilization statuses 108 associated with the one or more objects 102 do not meet and/or exceed one or more values associated with one or more sterilization levels 110 associated with one or more spaces 104. For example, in some embodiments, a space 104 surrounding a patient in a hospital may be associated with a medium sterilization level 110. Entry of an object 102, such as a physician, that is associated with a low sterilization status 108 into the space 104 surrounding the patient may cause one or more alert units 128 to indicate noncompliance of the object 102 with the space 104. For example, one or more alert units 128 may sound an alarm, flash a red light, or other such indicator.

At operation 908, the responding operation 620 may include generating one or more control signals 120 associated with one or more recording units 116. In some embodiments, one or more responding units 118 can generate one or more control signals 120 associated with one or more recording units 116. In some embodiments, one or more control signals 120 may be generated that indicate one or more positions of one or more objects 102 about one or more spaces 104. In some embodiments, such control signals 120 may be generated by one or more responding units 118. In some embodiments, the one or more control signals 120 may be recorded by one or more recording units 116. For example, in some embodiments, the positions of one or more surgical instruments may be tracked as they are moved about one or more spaces 104, such as in a hospital. In addition, one or more control signals 120 indicating the sterilization status 108 of one or more objects 102 may be generated. In some embodiments, such control signals 120 may be generated by one or more responding units 118. In some embodiments, these one or more control signals 120 may be recorded by one or more recording units 116. For example, in some embodiments, one or more control signals 120 associated with one or more sterilization statuses 108 associated with one or more surgical instruments can be generated by one or more responding units 118 and recorded by one or more recording units 116. Accordingly, one or more sterilization statuses 108 associated with one or more objects 102 can be tracked over time and recorded by one or more recording units 116. In some embodiments, one or more control signals 120 indicating the position and sterilization status 108 of one or more objects 102 about one or more spaces 104 can be generated. Such control signals 120 can be generated by one or more responding units 118 and recorded by one or more recording units 116. In some embodiments, such recorded control signals 120 may be used to monitor and/or report compliance or noncompliance with one or more protocols associated with one or more spaces 104. For example, a hospital may have an established protocol with regard to sterilization procedures used to sterilize surgical instruments. Records indicating when and where the surgical instruments were sterilized and where the instruments were transported may establish adherence to a sterilization protocol.

At operation 910, the responding operation 620 may include generating one or more control signals 120 associated with one or more sterilization units 126. In some embodiments, one or more responding units 118 can generate one or more control signals 120 associated with one or more sterilization units 126. In some embodiments, one or more control signals 120 may be generated that instruct one or more sterilization units 126 to sterilize one or more objects 102. For example, in some embodiments, one or more control signals 120 may be generated that indicate that one or more objects 102 are associated with one or more low sterilization statuses 108 and should be sterilized. Accordingly, the one or more control signals 120 may be received by one or more sterilization units 126 that will act to sterilize the one or more objects 102. In some embodiments, one or more control signals 120 may be generated that indicate that one or more objects 102 are associated with one or more high sterilization statuses 108 and should not be sterilized. Accordingly, the one or more control signals 120 may be received by one or more sterilization units 126 that will then refrain from sterilizing the one or more objects 102. In some embodiments, one or more responding units 118 can change the sterilization status 108 of one or more objects 102. For example, in some embodiments, one or more responding units 118 can change the sterilization status 108 of one or more non-sterile objects 102 to sterile after the one or more objects 102 have been sterilized. In some embodiments, one or more sterilization units 126 can change the sterilization status 108 of one or more objects 102. For example, in some embodiments, one or more sterilization units 126 can change the sterilization status 108 of one or more non-sterile objects 102 to sterile after the one or more objects 102 have been sterilized. For example, in some embodiments, a physician may initially be associated with a medium or higher sterilization status 108 upon entering into a first space 104 that is associated with a medium sterilization level 110 and that includes a first patient. Upon leaving the first space 104 after examining the first patient, one or more responding units 118 may change the sterilization status 108 associated with the physician to a low sterilization status 108. In some embodiments, the physician now associated with low sterilization status 108 after examining the first patient may be prohibited from entering into a second space 104 that is associated with a medium sterilization level 110 and that includes a second patient. One or more responding units 118 may generate one or more control signals 120 indicating that one or more sterilization agents need to be applied to the physician. Accordingly, one or more sterilization units 126 may be utilized to apply one or more sterilization agents to the physician. Upon completion of one or more sterilization procedures, the sterilization status 108 associated with the physician may be changed to a medium or higher sterilization status 108. In some embodiments, the sterilization status 108 associated with the physician may be changed by one or more responding units 118, by one or more sterilization units 126, and/or substantially any combination thereof. The physician may now be allowed entry into the second space 104 as the physician is now associated with a medium or higher sterilization status 108. Such methods may be utilized with numerous objects 102.

At operation 912, the responding operation 620 may include generating one or more control signals 120 associated with one or more control units 130. In some embodiments, one or more responding units 118 can generate one or more control signals 120 associated with one or more control units 130. Control units 130 may be configured in numerous ways. Examples of ways in which a control unit 130 may be configured include, but are not limited to, locks, doors, lights, switches, internet connections, transmitters, receivers, and the like. In some embodiments, one or more control signals 120 may be generated that are associated with one or more control units 130 that may be configured as part of a lock or a door. Accordingly, the one or more control signals 120 may control entry or exit from one or more spaces 104 having entry or exit that is controlled by such a lock or door. In some embodiments, one or more control units 130 may be configured as a switch.

Figure 10:
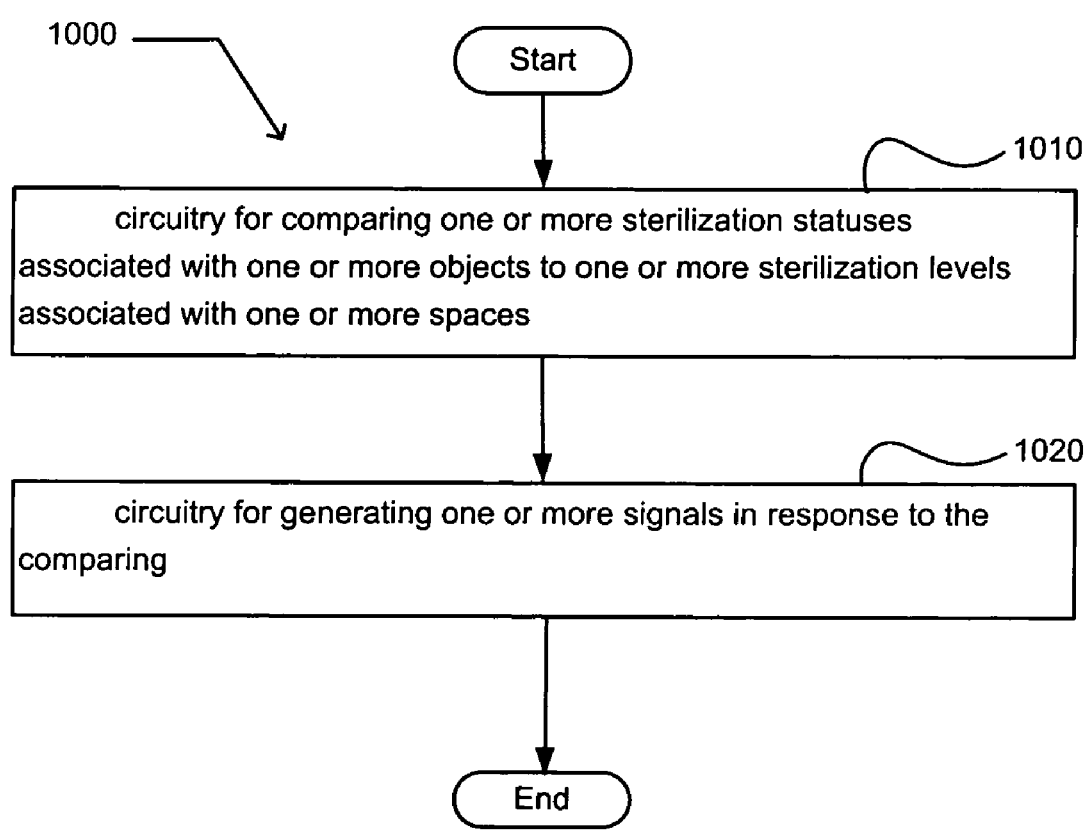
FIG. 10 illustrates an operational flow representing circuitry related to monitoring systems.

FIG. 10 illustrates an operational flow 1000 representing examples of operations that are related to the performance of a monitoring system. In FIG. 10 and in following figures that include various examples of operations used during performance of the sterilization method, discussion and explanation may be provided with respect to the above-described example of FIG. 1, and/or with respect to other examples and contexts. However, it should be understood that the operations may be executed in a number of other environments and contexts, and/or modified versions of FIG. I. Also, although the various operations are presented in the sequence(s) illustrated, it should be understood that the various operations may be performed in other orders than those which are illustrated, or may be performed concurrently.

After a start operation, the operational flow 1000 includes an operation 1010 involving circuitry for comparing one or more sterilization statuses associated with one or more objects to one or more sterilization levels associated with one or more spaces 104. In some embodiments, the circuitry may be used for determining if the one or more sterilization statuses 108 are within one or more compliance ranges associated with one or more sterilization levels 110. In some embodiments, the circuitry may be used for determining if the one or more sterilization statuses 108 are outside of one or more compliance ranges associated with one or more sterilization levels 110.

The operational flow 1000 also includes an operation 1020 involving circuitry for generating one or more signals in response to the comparing. In some embodiments, the circuitry may be used for generating one or more signals 112 associated with compliance of one or more sterilization statuses 108 with one or more sterilization levels I 10. In some embodiments, the circuitry may be used for generating one or more signals 112 associated with noncompliance of one or more sterilization statuses 108 with one or more sterilization levels 110. In some embodiments, the circuitry may be used for generating one or more signals 112 associated with entry of one or more objects 102 into one or more spaces 104. In some embodiments, the circuitry may be used for generating one or more signals 112 associated with exit of one or more objects 102 from one or more spaces 104. In some embodiments, the circuitry may be used for generating one or more signals 112 associated with one or more alert units 128. In some embodiments, the circuitry may be used for generating one or more signals 112 associated with one or more recording units 116. In some embodiments, the circuitry may be used for generating one or more signals 112 associated with one or more sterilization units 126. In some embodiments, the circuitry may be used for generating one or more signals 112 associated with one or more control units 130.

Figure 11:
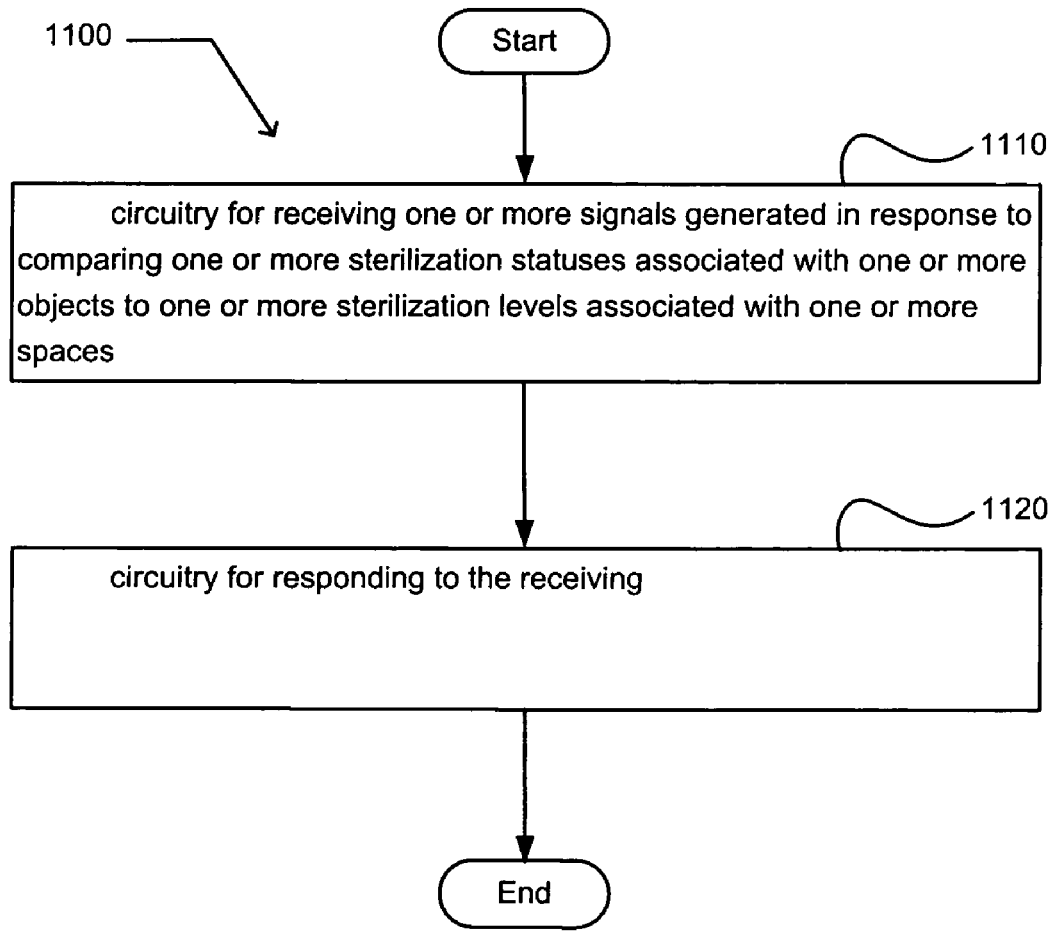
FIG. 11 illustrates an operational flow representing circuitry related to monitoring systems.

FIG. 11 illustrates an operational flow 1100 representing examples of operations that are related to the performance of a monitoring system. While FIG. 11 illustrates various examples of operations used during performance of the sterilization method, discussion and explanation may be provided with respect to the above-described example of FIG. 1, and/or with respect to other examples and contexts. However, it should be understood that the operations may be executed in a number of other environments and contexts, and/or modified versions of FIG. 1. Also, although the various operations are presented in the sequence(s) illustrated, it should be understood that the various operations may be performed in other orders than those which are illustrated, or may be performed concurrently.

After a start operation, the operational flow 1100 includes an operation 1110 involving circuitry for receiving one or more signals generated in response to comparing one or more sterilization statuses associated with one or more objects to one or more sterilization levels associated with one or more spaces 104. In some embodiments, the circuitry may be used for receiving one or more signals 112 associated with compliance of one or more sterilization statuses 108 with one or more sterilization levels 110. In some embodiments, the circuitry may be used for receiving the one or more signals 112 associated with noncompliance of one or more sterilization statuses 108 with one or more sterilization levels 110. In some embodiments, the circuitry may be used for receiving one or more signals 112 associated with entry of one or more objects 102 into one or more spaces 104. In some embodiments, the circuitry may be used for receiving one or more signals 112 associated with exit of one or more objects 102 from one or more spaces 104. In some embodiments, the circuitry may be used for receiving one or more signals 112 associated with one or more alert units 128. In some embodiments, the circuitry may be used for receiving the one or more signals 112 associated with one or more recording units 116. In some embodiments, the circuitry may be used for receiving one or more signals 112 associated with one or more sterilization units 126. In some embodiments, the circuitry may be used for receiving one or more signals 112 associated with one or more control units 130.

The operational flow 1100 also includes an operation 1120 involving circuitry for responding to the receiving. In some embodiments, the circuitry may be used for generating one or more control signals 120 associated with entry of one or more objects 102 into one or more spaces 104. In some embodiments, the circuitry may be used for generating one or more control signals 120 associated with exit of one or more objects 102 from one or more spaces 104. In some embodiments, the circuitry may be used for generating one or more control signals 120 associated with one or more alert units 128. In some embodiments, the circuitry may be used for generating one or more control signals 120 associated with one or more recording units 116. In some embodiments, the circuitry may be used for generating one or more control signals 120 associated with one or more sterilization units 126. In some embodiments, the circuitry may be used for generating one or more control signals 120 associated with one or more control units 130.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, those skilled in the art will recognize that the various embodiments described herein can be implemented, individually and/or collectively, by various types of electromechanical systems having a wide range of electrical components such as hardware, software, firmware, or virtually any combination thereof; and a wide range of components that may impart mechanical force or motion such as rigid bodies, spring or torsional bodies, hydraulics, and electro-magnetically actuated devices, or virtually any combination thereof. Consequently, as used herein "electro-mechanical system" includes, but is not limited to, electrical circuitry operably coupled with a transducer (e.g., an actuator, a motor, a piezoelectric crystal, etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), electrical circuitry forming a communications device (e.g., a modem, communications switch, or optical-electrical equipment), and any non-electrical analog thereto, such as optical or other analogs. Those skilled in the art will also appreciate that examples of electromechanical systems include but are not limited to a variety of consumer electronics systems, as well as other systems such as motorized transport systems, factory automation systems, security systems, and communication/computing systems. Those skilled in the art will recognize that electromechanical as used herein is not necessarily limited to a system that has both electrical and mechanical actuation except as context may dictate otherwise.

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

Those skilled in the art will recognize that it is common within the art to implement devices and/or processes and/or systems in the fashion(s) set forth herein, and thereafter use engineering and/or business practices to integrate such implemented devices and/or processes and/or systems into more comprehensive devices and/or processes and/or systems. That is, at least a portion of the devices and/or processes and/or systems described herein can be integrated into other devices and/or processes and/or systems via a reasonable amount of experimentation. Those having skill in the art will recognize that examples of such other devices and/or processes and/or systems might include—as appropriate to context and application—all or part of devices and/or processes and/or systems of (a) an air conveyance (e.g., an airplane, rocket, hovercraft, helicopter, etc.), (b) a ground conveyance (e.g., a car, truck, locomotive, tank, armored personnel carrier, etc.), (c) a building (e.g., a home, warehouse, office, etc.), (d) an appliance (e.g., a refrigerator, a washing machine, a dryer, etc.), (e) a communications system (e.g., a networked system, a telephone system, a voice-over IP system, etc.), (f) a business entity (e.g., an Internet Service Provider (ISP) entity such as Comcast Cable, Quest, Southwestern Bell, etc), or (g) a wired/wireless services entity such as Sprint, Cingular, Nextel, etc.), etc.

Although user 124 is shown/described herein as a single illustrated figure, those skilled in the art will appreciate that user 124 may be representative of a human user, a robotic user (e.g., computational entity), and/or substantially any combination thereof (e.g., a user may be assisted by one or more robotic agents). In addition, user 124, as set forth herein, although shown as a single entity may in fact be composed of two or more entities. Those skilled in the art will appreciate that, in general, the same may be said of "sender" and/or other entity-oriented terms as such terms are used herein.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated and/or in communication with each other can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

What is claimed is:

1. A method comprising:
    comparing one or more sterilization statuses associated with one or more objects to one or more sterilization levels associated with one or more spaces; and
    generating one or more signals in response to the comparing.

2. The method of claim 1, wherein the comparing one or more sterilization statuses associated with one or more objects to one or more sterilization levels associated with one or more spaces comprises:
    determining if the one or more sterilization statuses are within one or more compliance ranges associated with the one or more sterilization levels.

3. The method of claim 1, wherein the comparing one or more sterilization statuses associated with one or more objects to one or more sterilization levels associated with one or more spaces comprises:
    determining if the one or more sterilization statuses are outside of one or more compliance ranges associated with the one or more sterilization levels.

4. The method of claim 1, wherein the generating one or more signals in response to the comparing comprises:
    generating the one or more signals associated with compliance of the one or more sterilization statuses with the one or more sterilization levels.

5. The method of claim 1, wherein the generating one or more signals in response to the comparing comprises:
    generating the one or more signals associated with non-compliance of the one or more sterilization statuses with the one or more sterilization levels.

6. The method of claim 1, wherein the generating one or more signals in response to the comparing comprises:
    generating the one or more signals associated with entry of the one or more objects into the one or more spaces.

7. The method of claim 1, wherein the generating one or more signals in response to the comparing comprises:
    generating the one or more signals associated with exit of the one or more objects from the one or more spaces.

8. The method of claim 1, wherein the generating one or more signals in response to the comparing comprises:
    generating the one or more signals associated with one or more alert units.

9. The method of claim 1, wherein the generating one or more signals in response to the comparing comprises:
    generating the one or more signals associated with one or more recording units.

10. The method of claim 1, wherein the generating one or more signals in response to the comparing comprises:
    generating the one or more signals associated with one or more sterilization units.

11. The method of claim 1, wherein the generating one or more signals in response to the comparing comprises:
    generating the one or more signals associated with one or more control units.

* * * * *